(12) United States Patent
Sakurai et al.

(10) Patent No.: US 10,472,378 B2
(45) Date of Patent: Nov. 12, 2019

(54) TRANSPARENT FILM

(71) Applicant: SUMITOMO CHEMICAL COMPANY, LIMITED, Tokyo (JP)

(72) Inventors: Sayaka Sakurai, Osaka (JP); Tomonori Miyamoto, Osaka (JP); Ryu Takeko, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/522,562

(22) PCT Filed: Oct. 27, 2015

(86) PCT No.: PCT/JP2015/080264
§ 371 (c)(1),
(2) Date: Apr. 27, 2017

(87) PCT Pub. No.: WO2016/068138
PCT Pub. Date: May 6, 2016

(65) Prior Publication Data
US 2017/0313728 A1    Nov. 2, 2017

(30) Foreign Application Priority Data

Oct. 31, 2014    (JP) .................................. 2014-223651

(51) Int. Cl.
*C07F 7/18*     (2006.01)
*C08G 79/00*    (2006.01)
*C09D 183/04*   (2006.01)
*C09D 183/14*   (2006.01)
*C08G 77/04*    (2006.01)
*C07F 7/08*     (2006.01)
*C08G 77/50*    (2006.01)
*C08G 77/18*    (2006.01)

(52) U.S. Cl.
CPC .......... *C07F 7/1804* (2013.01); *C07F 7/0838* (2013.01); *C08G 77/04* (2013.01); *C08G 79/00* (2013.01); *C09D 183/04* (2013.01); *C09D 183/14* (2013.01); *C08G 77/18* (2013.01); *C08G 77/50* (2013.01)

(58) Field of Classification Search
CPC .............................. C07F 7/1808; C07F 7/1844
See application file for complete search history.

(56) References Cited

U.S. PATENT DOCUMENTS

| 651,753 A | 6/1900 | Fowlkes |
| 2,397,895 A | 4/1946 | Warrick |
| 3,450,672 A | 6/1969 | Merrill |
| 3,634,321 A | 1/1972 | Nugent et al. |
| 4,322,476 A | 3/1982 | Molari, Jr. |
| 4,895,286 A | 1/1990 | Derosa |
| 5,359,109 A | 10/1994 | Ritscher et al. |
| 6,511,753 B1 | 1/2003 | Teranishi et al. |
| 7,351,477 B2 | 4/2008 | Yamaya et al. |
| 7,785,715 B2 | 8/2010 | Tsumura et al. |
| 2002/0015800 A1 | 2/2002 | Miyamoto et al. |
| 2002/0064663 A1 | 5/2002 | Murphy et al. |
| 2004/0076840 A1 | 4/2004 | Akamatsu et al. |
| 2004/0152825 A1 | 8/2004 | Yamamoto et al. |
| 2005/0227092 A1 | 10/2005 | Yamaya et al. |
| 2007/0009657 A1 | 1/2007 | Zhang et al. |
| 2007/0053062 A1 | 3/2007 | Sasaki et al. |
| 2007/0141305 A1 | 6/2007 | Kasai et al. |
| 2008/0064814 A1 | 3/2008 | Yamamoto et al. |
| 2008/0090004 A1 | 4/2008 | Zhang et al. |
| 2011/0117344 A1* | 5/2011 | Chen ..................... C23C 14/022 428/213 |
| 2011/0165808 A1 | 7/2011 | Zimmermann et al. |
| 2013/0340992 A1 | 12/2013 | Akinaga et al. |

(Continued)

FOREIGN PATENT DOCUMENTS

CN    103443223 A    12/2013
EP    0565743 A1    10/1993

(Continued)

OTHER PUBLICATIONS

JP 2014 076924 machine translation (2014).*
JP 2013 222836 machine translation (2013).*
International Search Report, issued in PCT/JP2015/080264, dated Jan. 19, 2016.
Taiwanese Office Action and Search Report, dated Apr. 12, 2019, for Taiwanese Application No. 104135378, with an English translation.
Taiwanese Office Action and Search Report, dated Apr. 23, 2019, for Taiwanese Application No. 104135384, with an English translation.
Taiwanese Office Action and Search Report, dated Apr. 8, 2019, for Taiwanese Application No. 104135377, with an English translation.
AIST, "Transparent Coating Film Excellent in Oil Repellency," URL: http://www.aist.go.jp/aist_j/press_release/pr2012/pr20120313/pr20120313.html, Mar. 13, 2012, 5 pages, with partial English translation.

(Continued)

*Primary Examiner* — Kuo Liang Peng
(74) *Attorney, Agent, or Firm* — Birch, Stewart, Kolasch & Birch, LLP

(57) ABSTRACT

The object of the present invention is to attain water repellency as well as the heat resistance and the light resistance. the transparent film of the present invention comprises: a polysiloxane backbone; and a trialkylsilyl containing molecular chain bonded to a part of silicon atoms forming the polysiloxane backbone, wherein alkyl groups in the trialkylsilyl containing molecular chain may be replaced by fluoroalkyl groups, and the transparent film satisfies at least one of the relationships of:

$(B_H-A_0)/A_0 \times 100(\%) \geq -27(\%)$; and $(B_L-A_0)/A_0 \times 100(\%) \geq -15(\%)$, provided that $A_0$ is an initial contact angle of a liquid droplet on the transparent film, $B_H$ is a contact angle of a liquid droplet on the transparent film incubated at 200° C. for 24 hours, and $B_L$ is a contact angle of a liquid droplet on the transparent film irradiated by a xenon lamp with an intensity of 250 W for 100 hours.

17 Claims, 1 Drawing Sheet

(56) References Cited

U.S. PATENT DOCUMENTS

| | | | |
|---|---|---|---|
| 2015/0021643 | A1 | 1/2015 | Kurino et al. |
| 2015/0118502 | A1 | 4/2015 | Mitsuhashi et al. |
| 2016/0032146 | A1 | 2/2016 | Hozumi et al. |
| 2017/0015842 | A1 | 1/2017 | Hozumi et al. |

FOREIGN PATENT DOCUMENTS

| | | | |
|---|---|---|---|
| JP | 5-148451 A | | 6/1993 |
| JP | 6-32991 A | | 2/1994 |
| JP | 7-48560 A | | 2/1995 |
| JP | 7-161453 A | | 6/1995 |
| JP | 7-179480 A | | 7/1995 |
| JP | 9-157636 A | | 6/1997 |
| JP | 9-309889 A | | 12/1997 |
| JP | 10-326559 A | | 12/1998 |
| JP | 11-92714 A | | 4/1999 |
| JP | 11-218926 A | | 8/1999 |
| JP | 2000-17229 A | | 1/2000 |
| JP | 2000-80354 A | | 3/2000 |
| JP | 2000-182513 A | | 6/2000 |
| JP | 2000-195415 A | | 7/2000 |
| JP | 2002-256258 A | | 9/2002 |
| JP | 2004-122106 A | | 4/2004 |
| JP | 2005-120236 A | | 5/2005 |
| JP | 2008-96516 A | | 4/2008 |
| JP | 2008-137858 A | | 6/2008 |
| JP | 2009-521551 A | | 6/2009 |
| JP | 2010-222703 A | | 10/2010 |
| JP | 2010-248468 A | | 11/2010 |
| JP | 2011-111509 A | | 6/2011 |
| JP | 2011-174001 A | | 9/2011 |
| JP | 2012-17394 A | | 1/2012 |
| JP | 2012-46765 A | | 3/2012 |
| JP | 2012-214588 A | | 11/2012 |
| JP | 2013-155375 A | | 8/2013 |
| JP | 2013-173939 A | | 9/2013 |
| JP | 2013-213181 A | | 10/2013 |
| JP | 2013222836 | * | 10/2013 |
| JP | 2014-15609 A | | 1/2014 |
| JP | 2014-37548 A | | 2/2014 |
| JP | 5472543 B2 | | 4/2014 |
| JP | 2014 076924 | * | 5/2014 |
| JP | 2014-76924 A | | 5/2014 |
| JP | 2014-185334 A | | 10/2014 |
| KR | 10-2006-0045524 A | | 5/2006 |
| TW | 201414769 A | | 4/2014 |
| WO | WO 2010/074264 A1 | | 7/2010 |
| WO | WO 2012/137976 A1 | | 10/2012 |

OTHER PUBLICATIONS

Chinese Office Action for Chinese Application No. 201580009221.8, dated Apr. 12, 2017, with English translation.
Extended European Search Report for European Application No. 15751325.0, dated Dec. 9, 2016.
Gao et al., "Contact Angle Hysteresis Explained," Langmuir, vol. 22, No. 14, 2006 (published online Jun. 3, 2006), pp. 6234-6237.
International Search Report (Form PCT/ISA/210) for International Application No. PCT/JP2015/054626, dated May 26, 2015.
International Search Report (Form PCT/ISA/210) for International Application No. PCT/JP2015/080176, dated Jan. 19, 2016.
International Search Report (Form PCT/ISA/210) for International Application No. PCT/JP2015/081422, dated Jan. 19, 2016.
International Search Report (Form PCT/ISA/210) for International Application No. PCT/JP2015/081504, dated Jan. 19, 2016.
International Search Report (Form PCT/ISA/210), for International Application No. PCT/JP2015/080209, dated Jan. 19, 2016.
Japanese Office Action for Japanese Application No. 2014-032316, dated Mar. 13, 2018, with English translation.
Korean Office Action for Korean Application No. 10-2016-7025075, dated Dec. 13, 2017, with English translation.
Park et al., "Long Perfluoroalkyl Chains are not Required for Dynamically Oleophobic Surfaces\," Green Chemistry, vol. 15, 2013, pp. 100-104.
Synquest Laboratories, "(3,3,3-Trifluoropropyl)dimethylchlorosilane," Product Sheet, URL: http://www.synquestlabs.com/product/id/27794.html, 2010, 1 page.
U.S. Office Action for U.S. Appl. No. 15/119,437, dated Feb. 6, 2018.
U.S. Office Action for U.S. Appl. No. 15/119,437, dated Jun. 6, 2018.
U.S. Office Action for U.S. Appl. No. 15/522,626, dated Oct. 11, 2018.
U.S. Office Action for U.S. Appl. No. 15/525,177, dated Jun. 20, 2018.
U.S. Office Action for U.S. Appl. No. 15/525,188, dated Oct. 5, 2018.
Urata et al., "How to Reduce Resistance to Movement of Alkane Liquid Drops Across Tilted Surfaces Without Relying on Surface Roughening and Perfluorination," Langmuir, vol. 28, Nov. 30, 2012, pp. 17681-17689.
Urata et al., "Smooth, Transparent and Nonperfluorinated Surfaces Exhibiting Unusual Contact Angle Behavior Toward Organic Liquids," RSC Advances, vol. 2, 2012, pp. 9805-9808.
Urata et al., "Unusual Dynamic Dewetting Behavior of Smooth Perfluorinated Hybrid Films: Potential Advantages over Conventional Textured and Liquid-Infused Perfluorinated Surfaces," Langmuir, vol. 29, Sep. 11, 2013, pp. 12472-12482.
Urata et al., "Why Can Organic Liquids Move Easily on Smooth Alkyl-Terminated Surfaces?" Langmuir, vol. 30, Mar. 24, 2014, pp. 4049-4055.
U.S. Office Action for U.S. Appl. No. 15/522,584, dated Jun. 15, 2018.
Taiwanese Office Action and Search Report dated Mar. 5, 2019 for Application No. 104136832, with an English translation.
Chinese Office Action (including an English translation thereof) issued in the Chinese Patent Application No. 201580059039.3 dated Nov. 1, 2018.
Chinese Office Action (including an English translation thereof) issued in the Chinese Patent Application No. 201580059081.5 dated Oct. 24, 2018.
Chinese Office Action (including an English translation thereof) issued in the Chinese Patent Application No. 201580059125.4 dated Nov. 29, 2018.
Chinese Office Action (including an English translation thereof) issued in the Chinese Patent Application No. 201580060808.1 dated Oct. 31, 2018.
Chinese Office Action (including an English translation thereof) issued in the Chinese Patent Application No. 201580061118.8 dated Nov. 29, 2018.
Taiwanese Office Action and Search Report (including an English translation thereof) issued in the Taiwanese Patent Application No. 104136831 dated Jun. 13, 2019.
U.S. Office Action for U.S. Appl. No. 15/522,626, dated Jul. 8, 2019.
Chinese Office Action and Search Report dated Jul. 16, 2019 for Application No. 201580059039.3, along with an English translation of the Office Action.
Japanese Office Action for Japanese Application No. 2016-556570, dated Sep. 10, 2019, with English translation.
Japanese Office Action for Japanese Application No. 2016-556576, dated Sep. 10, 2019, with English translation.
Japanese Office Action for Japanese Application No. 2016-556583, dated Sep. 10, 2019, with English translation.
Japanese Office Action for Japanese Application No. 2016-559029, dated Sep. 10, 2019, with English translation.
Japanese Office Action for Japanese Application No. 2016-559042, dated Sep. 10, 2019, with English translation.

* cited by examiner

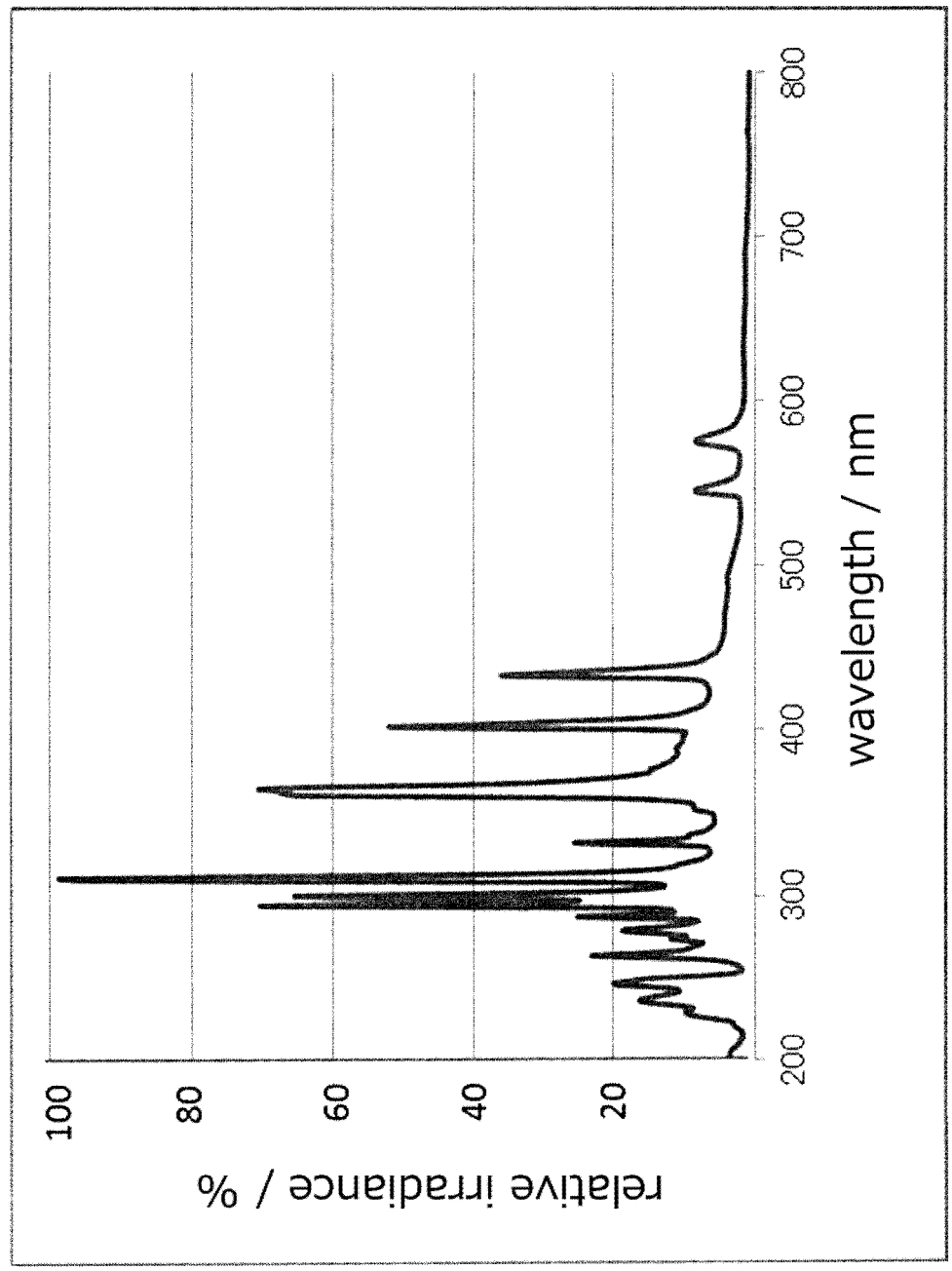

TRANSPARENT FILM

TECHNICAL FIELD

The present invention relates to a transparent film capable of imparting water repellency to various kinds of substrates.

BACKGROUND ART

In various kinds of display devices, optical elements, semiconductor elements, building materials, automobile components and nanoimprint techniques, deposition of liquid droplets on a surface of a substrate may cause a problem of contamination and corrosion of the substrate, or further the deterioration in the performance due to the contamination and corrosion. Therefore, in these fields the substrate surface is required to have good water repellency. Particularly, it is required not only the prevention of deposition of liquid droplets on the substrate surface, but also the ease of removing deposited liquid droplets is required.

As a film capable of causing even a very small water droplet to slide down with a small inclination angle, Patent Document 1 proposes a film obtained by co-hydrolysis/condensation polymerization of an organosilane and a metal alkoxide in a solution containing an organic solvent and water.

PRIOR ART DOCUMENT

Patent Document

Patent Document 1: JP 2013-213181 A

SUMMARY OF THE INVENTION

Problems to be Solved by the Invention

The present inventors found that the film described in Patent Document 1 may have insufficient heat resistance and light resistance. When heat resistance and light resistance are insufficient, a treated film is easily degraded, resulting in deterioration of water repellency. The object of the present invention is to attain water repellency as well as the heat resistance and the light resistance (hereinafter, heat resistance and light resistance are collectively referred to as "weather resistance").

Solutions to the Problems

The present inventors extensively studied in view of the situations described above, and resultantly found that when a change in contact angle before and after thermal history or before and after photoirradiation is adjusted to a specific range, a transparent film attains water repellency as well as heat resistance and light resistance (weather resistance), thereby leading to the completion of the present invention.

The transparent film of the present invention comprises:
a polysiloxane backbone; and
a trialkylsilyl containing molecular chain bonded to a part of silicon atoms forming the polysiloxane backbone,
wherein alkyl groups in the trialkylsilyl containing molecular chain may be replaced by fluoroalkyl groups, and
the transparent film satisfies at least one of the relationships of:

$$(B_H - A_0)/A_0 \times 100(\%) \geq -27(\%); \text{ and}$$

$$(B_L - A_0)/A_0 \times 100(\%) \geq -15(\%),$$

provided that $A_0$ is an initial contact angle of a liquid droplet on the transparent film, $B_H$ is a contact angle of a liquid droplet on the transparent film incubated at 200° C. for 24 hours, and $B_L$ is a contact angle of a liquid droplet on the transparent film irradiated by a xenon lamp with an intensity of 250 W for 100 hours.

The transparent film of the present invention comprises:
a polysiloxane backbone; and
a trialkylsilyl containing molecular chain bonded to a part of silicon atoms forming the polysiloxane backbone,
wherein alkyl groups in the trialkylsilyl containing molecular chain may be replaced by fluoroalkyl groups, and
the transparent film satisfies a relationship represented by a formula below:

$$(B_{z1} - A_1)/A_1 \times 100(\%) \geq -9(\%)$$

provided that $A_1$ is an initial contact angle of a liquid droplet on the transparent film, and $B_{z1}$ is a contact angle of the liquid droplet on the transparent film irradiated by a mercury lamp having an emission line in a region of not more than 300 nm with an intensity at an irradiated surface of 200±10 mW/cm² at a temperature of 20 to 40° C. and a humidity of 30 to 75% for 4 hours under an air atmosphere.

The trialkylsilyl containing molecular chain is preferably represented by a formula (s1) below:

$$*\!-\!R^{s2}\!-\!Si(R^{s1})_3 \tag{s1}$$

wherein each of $R^{s1}$ independently represents a hydrocarbon group or a trialkylsilyloxy group, provided that these hydrocarbon groups are alkyl groups when all $R^{s1}$ are hydrocarbon groups;

$R^{s2}$ represents a dialkylsiloxane chain and an oxygen atom in the dialkylsiloxane chain may be replaced by a divalent hydrocarbon group and a part of methylene groups ($-CH_2-$) in the divalent hydrocarbon group may be replaced by oxygen atoms; and

* represents a bond with silicon atom.

The trialkylsilyl containing molecular chain is preferably represented by a formula (s1-1) below:

$$*\!-\!(O\!-\!Si(R^{s3})_2)_n\!-\!(R^{s4})_m\!-\!Si(O\!-\!Si(R^{s5})_3)_3 \tag{s1-1}$$

wherein each of $R^{s3}$ independently represents an alkyl group with a carbon number of not less than 1 and not more than 4;

$R^{s4}$ represents a divalent hydrocarbon group with a carbon number of not less than 1 and not more than 10, and a methylene group ($-CH_2-$) in $R^{s4}$ may be replaced by an oxygen atom;

each of $R^{s5}$ independently represents an alkyl group with a carbon number of not less than 1 and not more than 4;

m1 and n1 independently represent an integer of not less than 0; and

* represents a bond with silicon atom;

provided that occurrence order of the repeating units parenthesized with the subscripts of n1 and m1 is arbitrary in the formula.

The transparent film preferably comprises further a unit including a metal atom and a group bonded to the metal atom selected from a siloxane containing group and hydroxy group, wherein the metal atom is selected from trivalent and tetravalent metal atoms capable of forming a metal alkoxide, the number of elements in the siloxane containing group is smaller than the number of elements in the molecular chain of the trialkylsilyl containing molecular chain, and the unit is bonded to the polysiloxane backbone at a position of the metal atom.

The transparent film preferably comprises a structure (B) represented by a formula (2-1) below:

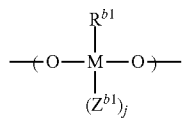
(2)

wherein $R^{b1}$ represents the siloxane containing group, hydroxy group or —O— group, $Z^{b1}$ represents a hydrolyzable group, hydroxy group or —O— group, and $R^{b1}$ and $Z^{b1}$ may be the same or different among a plurality of formulae (2-I);

M represents the trivalent or tetravalent metal atom capable of forming the metal alkoxide; and j represents an integer of 0 or 1 depending on M.

M preferably represents Al, Si, Ti or Zr.

An abundance ratio of the structure (B) to a structure (A) as structure (B)/structure (A) is preferably not less than 0.1 and not more than 80 in terms of moles wherein structure (A) comprises a trialkylsilyl containing molecular chain bonded to a silicon atom.

The initial contact angle of the liquid droplet on the transparent film is preferably not less than 95° in the transparent film of the present invention.

The coating composition preferably comprises an organosilicon compound (a) and a metal compound (b), wherein the organosilicon compound (a) comprises at least one trialkylsilyl containing molecular chain and at least one hydrolyzable group bonded to a silicon atom, and the metal compound (b) comprises a hydrolyzable group bonded to a metal atom.

The metal compound (b) is preferably at least one selected from a compound represented by a formula (II-1) below and a hydrolysis condensation product of the compound, and a molar ratio of the metal compound (b) to the organosilicon compound (a) as metal compound (b)/organosilicon compound (a) is not less than 10:

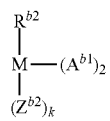
(II-1)

wherein M represents a trivalent or tetravalent metal atom capable of forming a metal alkoxide;

$A^{b1}$ represents a hydrolyzable group;

w$Z^{b2}$ represents a siloxane containing group, a hydrocarbon chain-containing group or a hydrolyzable group;

$R^{b2}$ represents a siloxane containing group, a hydrocarbon chain-containing group or a hydrolyzable group, $R^{b2}$ and $Z^{b2}$ may be the same or different when $R^{b2}$ and $Z^{b2}$ represent a siloxane containing group or a hydrocarbon chain-containing group, and $R^{b2}$ and $A^{b1}$ may be the same or different when $Z^{b2}$ represents a hydrolyzable group, and $R^{b2}$ and $Z^{b2}$ may be the same or different among a plurality of formulae (II-1);

k represents an integer of 0 or 1 depending on M; and wherein the siloxane containing group comprises elements in a number smaller than the number of elements forming the trialkylsilyl containing molecular chain in the organosilicon compound (a) when $R^{b2}$ represents a siloxane containing group.

The organosilicon compound (a) is preferably represented by a formula (I-I) below:

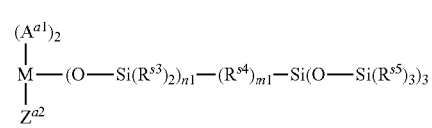
(I-I)

wherein each of $A^{a1}$ independently represents the hydrolyzable group;

$Z^{a2}$ represents a trialkylsilyl containing molecular chain, a hydrocarbon chain-containing group, a siloxane containing group or a hydrolyzable group, and $Z^{a2}$ and $A^{a1}$ may be the same or different when $Z^{a2}$ represents a hydrolyzable group, and $R^a$ and $Z^{a2}$ may be the same or different among a plurality of formulae (I-I);

each of $R^{s3}$ independently represents an alkyl group with a carbon number of not less than 1 and not more than 4;

$R^{s4}$ represents a divalent hydrocarbon group with a carbon number of not less than 1 and not more than 10, and a methylene group (—$CH_2$—) in $R^{s4}$ may be replaced by an oxygen atom;

each of $R^{s5}$ independently represents an alkyl group with a carbon number of not less than 1 and not more than 4; and m1 and n1 independently represent an integer of not less than 0;

provided that occurrence order of the repeating units parenthesized with the subscripts n1 and m1 is arbitrary in the formula.

A compound represented by a formula (I-I) below is also embraced within the scope of the present invention:

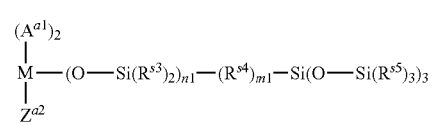
(I-I)

wherein each of $A^{a1}$ independently represents a hydrolyzable group;

$Z^{a2}$ represents a trialkylsilyl containing molecular chain, a hydrocarbon chain-containing group, a siloxane containing group or a hydrolyzable group, and $Z^{a2}$ and $A^{a1}$ may be the same or different when $Z^{a2}$ represents a hydrolyzable group, and $R^a$ and $Z^{a2}$ may be the same or different among a plurality of formulae (I-I);

each of $R^{s3}$ independently represents an alkyl group with a carbon number of not less than 1 and not more than 4;

$R^{s4}$ represents a divalent hydrocarbon group with a carbon number of not less than 1 and not more than 10, and a methylene group (—$CH_2$—) in $R^{s4}$ may be replaced by an oxygen atom;

each of $R^{s5}$ independently represents an alkyl group with a carbon number of not less than 1 and not more than 4; and m1 and n1 independently represent an integer of not less than 0;

provided that occurrence order of the repeating units parenthesized with the subscripts of n1 and m1 is arbitrary in the formula.

Effects of the Invention

The transparent film of the present invention attains water/oil repellency as well as light resistance and heat resistance because a change in the contact angle before and after thermal history or before and after photoirradiation is adjusted to a specific range.

BRIEF DESCRIPTION OF THE DRAWING

FIG. 1 shows a spectral irradiance for "SP-9 250DB" manufactured by USHIO INC.

MODE FOR CARRYING OUT THE INVENTION

In the transparent film of the present invention, a change in the contact angle before and after thermal history or before and after photoirradiation is suppressed. According to the present invention, a transparent film is found to be capable of attaining water/oil repellency as well as light resistance and heat resistance is obtained when a change in contact angle is adjusted to a specific range. The transparent film of the present invention comprises: a polysiloxane backbone; and a trialkylsilyl containing molecular chain bonded to a part of silicon atoms forming the polysiloxane backbone, wherein alkyl groups in the trialkylsilyl containing molecular chain may be replaced by fluoroalkyl groups, and the transparent film satisfies at least one of the relationships of:

$$(B_H-A_0)/A_0 \times 100(\%) \geq -27(\%); \text{ and}$$

$(B_L-A_0)/A_0 \times 100(\%) \geq -15(\%)$, provided that $A_0$ is an initial contact angle of a liquid droplet on the transparent film, $B_H$ is a contact angle of a liquid droplet on the transparent film incubated at 200° C. for 24 hours, and $B_L$ is a contact angle of a liquid droplet on the transparent film irradiated by a xenon lamp with an intensity of 250 W for 100 hours.

In the description below, a test of incubation at 200° C. for 24 hours is defined as a heat resistance test, a test of irradiation by a xenon lamp with an intensity of 250 W for 100 hours is defined as a light resistance test, the value of $(B_H-A_0)/A_0 \times 100(\%)$ is defined as a contact angle change ratio $D_H$ after a heat resistance test, and the value of $(B_L-A_0)/A_0 \times 100(\%)$ is defined as a contact angle change ratio $D_L$ after a light resistance test.

The contact angle is a value measured by a θ/2 method using water in an amount of 3 μL. The initial contact angle $A_0$ is a contact angle of a transparent film that is not subjected to a heat resistance test and a light resistance test.

The contact angle change ratio $D_H$ after a heat resistance test is not less than −27%, preferably not less than −27.0%, more preferably not less than −18%, still more preferably not less than −10%, further preferably not less than −5%, and is normally, preferably not more than 10%. When the contact angle change ratio $D_H$ after a heat resistance test is in the range as described above, both water/oil resistance and weather resistance can be attained.

The contact angle change ratio $D_L$ after a light resistance test is not less than −15%, preferably not less than −15.0%, more preferably not less than −8%, further preferably not less than −3%, and is normally, preferably not more than 10%. When the contact angle change ratio $D_L$ after a light resistance test is in a range as described above, both water/oil resistance and weather resistance can be attained.

The initial contact angle $A_0$ is preferably not less than 80°, more preferably not less than 90°, still more preferably not less than 95°, further preferably not less than 98°, especially preferably not less than 100°, and is normally, preferably not more than 180°.

The contact angle $B_H$ after a heat resistance test is preferably not less than 75°, more preferably not less than 85°, further preferably not less than 90°, and is normally, preferably not more than 180°.

The contact angle $B_L$ after a light resistance test is preferably not less than 75°, more preferably not less than 90°, further preferably not less than 95°, and is normally, preferably not more than 180°.

The transparent film of the present invention preferably comprises: a polysiloxane backbone; and a trialkylsilyl containing molecular chain bonded to a part of silicon atoms forming the polysiloxane backbone, wherein alkyl groups in the trialkylsilyl containing molecular chain may be replaced by fluoroalkyl groups, and the transparent film satisfies a relationship represented by a formula below:

$$(B_{z1}-A_1)/A_1 \times 100(\%) \geq -9(\%)$$

provided that $A_1$ is an initial contact angle of a liquid droplet on the transparent film, and $B_{z1}$, is a contact angle of the liquid droplet on the transparent film irradiated by a mercury lamp having an emission line in a region of not more than 300 nm with an intensity at an irradiated surface of 200±10 mW/cm² for 4 hours under an air atmosphere.

The transparent film of the present invention is excellent particularly in the light resistance, and even when the transparent film is irradiated with high intensity light, its water/oil-repellency characteristic is hardly deteriorated. The contact angle change ratio as $(B_{z1}-A_1)/A_1 \times 100(\%)$ before and after the irradiation for 4 hours is preferably not less than −9.0%, more preferably not less than −7%, further preferably not less than −5%, especially preferably not less than −3%.

In the transparent film of the present invention, it is preferred that the contact angle change ratio as $(B_{z2}-A_1)/A_1 \times 100(\%)$ satisfies a relationship represented by the following formula:

$$(B_{z2}-A_1)/A_1 \times 100(\%) \geq -18(\%)$$

provided that $B_{z2}$ is a contact angle of the liquid droplet after the irradiation by a mercury lamp having an emission line in a (wavelength) region of not more than 300 nm with the intensity at an irradiated surface of 200±10 mW/cm², for 6 hours The contact angle change ratio as $(B_{z2}-A_1)/A_1 \times 100(\%)$ before and after the irradiation for 6 hours is more preferably not less than −16%, still more preferably not less than −10%, further preferably not less than −7%, especially preferably not less than −5%, and may be, for example, not more than −1%.

Preferably, the irradiation of light from the mercury lamp is performed under an air atmosphere, the temperature is not less than 20° C. and not more than 40° C., and the humidity is not less than 30% and not more than 75%.

Examples of the mercury lamp having an emission line in a (wavelength) region of not more than 300 nm include "SP-9 250DB" manufactured by USHIO INC. and equivalents thereof.

The thickness of the transparent film of the present invention is, for example, 0.2 to 2000 nm, preferably 0.5 to 1000 nm, more preferably 1 to 80 nm. The thickness of the transparent film may be not more than 200 nm, or not more than 100 nm, or even not more than 40 nm.

The total light transmittance of the transparent film of the present invention, which is measured in accordance with JIS K 7361-1 or JIS K 7375, is preferably not less than 70%, more preferably not less than 80%, further preferably not less than 85%.

The contact angle change ratio after a heat resistance test or a light resistance test may be adjusted to the abovementioned range by forming the transparent film with a polysiloxane backbone, and bonding a trialkylsilyl containing molecular chain to some of silicon atoms forming the polysiloxane backbone. Alkyl groups in the trialkylsilyl containing molecular chain may be wholly replaced by fluoroalkyl groups.

In the present invention, the polysiloxane backbone represents a backbone in which silicon atoms and oxygen atoms are alternately arranged, and silicon atoms are three-dimensionally connected through oxygen atoms. The polysiloxane backbone improves the chemical and physical durability and transparency of the film. The polysiloxane backbone preferably comprises a three-dimensional network structure including a Si—O—Si bond, and the polysiloxane backbone may comprise a structure in which a divalent hydrocarbon group is interposed between silicon atoms.

The transparent film of the present invention comprises a structure (A) in which a trialkylsilyl containing molecular chain is bonded to a part of silicon atoms forming the polysiloxane backbone.

The trialkylsilyl containing molecular chain is a monovalent group having a molecular chain to which a trialkylsilyl group is bonded, and since a trialkylsilyl group is bonded to the molecular chain, water/oil repellency at a transparent film interface (surface) improves. Particularly, existence of a trialkylsilyl containing molecular chain reduces friction between a liquid droplet (water droplet, oil droplet or the like) and the transparent film, so that the liquid droplet easily moves. Existence of a trialkylsilyl group further increases chemical and physical durability, leading to improvement of heat resistance and light resistance. The water/oil repellency at a transparent film interface (surface) also improves in the case where the alkyl groups in the trialkylsilyl group are replaced by fluoroalkyl groups.

The carbon number of the alkyl group included in the trialkylsilyl group is preferably not less than 1 and not more than 4, more preferably not less than 1 and not more than 3, further preferably not less than 1 and not more than 2. The total carbon number of three alkyl groups included in the trialkylsilyl group is preferably not more than 9, more preferably not more than 6, further preferably not more than 4.

Examples of the alkyl group included in the trialkylsilyl group include methyl group, ethyl group, propyl group and butyl group. The three alkyl groups in the trialkylsilyl group may be the same or different, and preferably the same. Preferably, the trialkylsilyl group includes at least one methyl group, more preferably two or more methyl groups. Especially preferably, all the three alkyl groups are methyl groups.

Specific examples of the trialkylsilyl group include trialkylsilyl groups in which one methyl group is bonded to a silicon atom, such as methyldiethylsilyl group, methylethylpropylsilyl group, methylethylbutylsilyl group, methyldipropylsilyl group, methylpropylbutylsilyl group and methyldibutylsilyl group; trialkylsilyl groups in which two methyl groups are bonded to a silicon atom, such as dimethylethylsilyl group, dimethylpropylsilyl group and dimethylbutylsilyl group; and trimethylsilyl group.

A part or all of the alkyl groups included in the trialkylsilyl group may be replaced in their entirety by trialkylsilyloxy groups. Even in this case, the trialkylsilyl containing molecular chain comprises a trialkylsilyl group. Examples of the replacing trialkylsilyloxy group include groups with oxygen atoms bonded to a silicon atom in a trialkylsilyl group selected from the groups described above, and the replacing trialkylsilyloxy group is preferably a trialkylsilyloxy group with one or more methyl groups bonded to a silicon atom, more preferably a trialkylsilyloxy group with two or more methyl groups bonded to a silicon atom, especially preferably a trialkylsilyloxy group with three methyl groups bonded to a silicon atom.

Here, the number of trialkylsilyl groups included in the trialkylsilyl containing molecular chain is preferably not less than 2, more preferably not less than 3.

Alkyl groups in the trialkylsilyl group and alkyl groups in trialkylsilyloxy groups that may replace the alkyl groups in the trialkylsilyl group may be replaced in their entirety by fluoroalkyl groups. Examples of the fluoroalkyl group include groups in which at least some of hydrogen atoms in the alkyl group are replaced by fluorine atoms, and the carbon number of the fluoroalkyl group is preferably not less than 1 and not more than 4, more preferably not less than 1 and not more than 3, further preferably not less than 1 and not more than 2. For example, the number of replacing fluorine atoms is preferably not less than 1, and preferably not more than $2 \times A + 1$ where A is the number of carbon atoms. Specific examples of the fluoroalkyl group include monofluoromethyl group, difluoromethyl group, trifluoromethyl group (perfluoromethyl group), monofluoroethyl group, difluoroethyl group, trifluoroethyl group, tetrafluoroethyl group, pentafluoroethyl group (perfluoroethyl group), monofluoropropyl group, difluoropropyl group, trifluoropropyl group, tetrafluoropropyl group, pentafluoropropyl group, hexafluoropropyl group, heptafluoropropyl group (perfluoropropyl group), monofluorobutyl group, difluorobutyl group, trifluorobutyl group, tetrafluorobutyl group, pentafluorobutyl group, hexafluorobutyl group, heptafluorobutyl group, octafluorobutyl group and nonafluorobutyl group (perfluorobutyl group).

When alkyl groups are replaced by fluoroalkyl groups, the number of the replacing fluoroalkyl groups can be appropriately selected within the range of 1 to 3 per one silicon atom.

It is preferred that in the trialkylsilyl containing molecular chain, the trialkylsilyl group is bonded to one end (free end side) of the molecular chain, particularly to one end (free end side) of the main chain. The water/oil repellency of the transparent film thereby improves, and the heat resistance and the light resistance of the transparent film also improves.

The molecular chain to which the trialkylsilyl group is bonded is preferably linear or branched, more preferably linear. The molecular chain is preferably a dialkylsiloxane chain, more preferably a linear dialkylsiloxane chain. Here, in the present invention, the dialkylsiloxane chain means a molecular chain in which silicon atoms that is bonded by two alkyl groups and oxygen atoms are alternately connected. The carbon number of the alkyl group bonded to a silicon atom in the dialkylsiloxane chain is preferably not less than 1 and not more than 4, more preferably not less than 1 and not more than 3, further preferably not less than 1 and not more than 2. Specific examples of the alkyl group bonded to a silicon atom in the dialkylsiloxane chain include methyl group, ethyl group, propyl group and butyl group.

Specific examples of the dialkylsiloxane chain include (poly)dimethylsiloxane chains and (poly)diethylsiloxane chains.

In the dialkylsiloxane chain, the number of repeating dialkylsilyloxy groups is not less than 1, and preferably not more than 100, more preferably not more than 80, further preferably not more than 50, especially preferably not more than 20, most preferably not more than 15.

A plurality of dialkylsiloxane chains as described above may be connected in series. A part of the series structure may include a divalent hydrocarbon group. Specifically, a part of oxygen atoms in the dialkylsiloxane chain may be replaced by divalent hydrocarbon groups. Even when a part of the dialkylsiloxane chain is replaced by hydrocarbon groups, the other part remains as a dialkylsiloxane chain, and therefore the transparent film exhibits high chemical and physical durability and excellent heat resistance and light resistance. The carbon number of the divalent hydrocarbon group is preferably not more than 10, more preferably not more than 6, further preferably not more than 4, and is normally, preferably not less than 1. The divalent hydrocarbon group is preferably in a chain form, and the chain may be linear or branched. The divalent hydrocarbon group is preferably a divalent aliphatic hydrocarbon group, more preferably a divalent saturated aliphatic hydrocarbon group. Specific examples of the divalent hydrocarbon group include divalent saturated aliphatic hydrocarbon groups such as methylene group, ethylene group, propylene group and butylene group.

The divalent hydrocarbon group included in the dialkylsiloxane chain may be a group in which a part of methylene groups (—$CH_2$—) of the hydrocarbon chain are replaced by oxygen atoms as necessary. Two continuous methylene groups (—$CH_2$—) are not simultaneously replaced by oxygen atoms, and it is preferred that methylene groups (—$CH_2$—) adjacent to Si atoms are not replaced by oxygen atoms. Specific examples of the group in which a part of hydrocarbon groups are replaced by oxygen atoms may include groups having (poly)ethylene glycol units and groups having (poly)propylene glycol units.

Preferably, the dialkylsiloxane chain is composed only of repeating dialkylsilyloxy groups. When the dialkylsiloxane chain is composed only of repeating dialkylsilyloxy groups, the light resistance of the transparent film further improves.

Examples of the molecular chain included in the trialkylsilyl containing molecular chain may include molecular chains represented by the following formulae. In the formulae, the symbol * on the right side represents a bond that is bonded to a silicon atom forming a polysiloxane backbone, and the symbol * on the left side represents a bond that is bonded to a trialkylsilyl group.

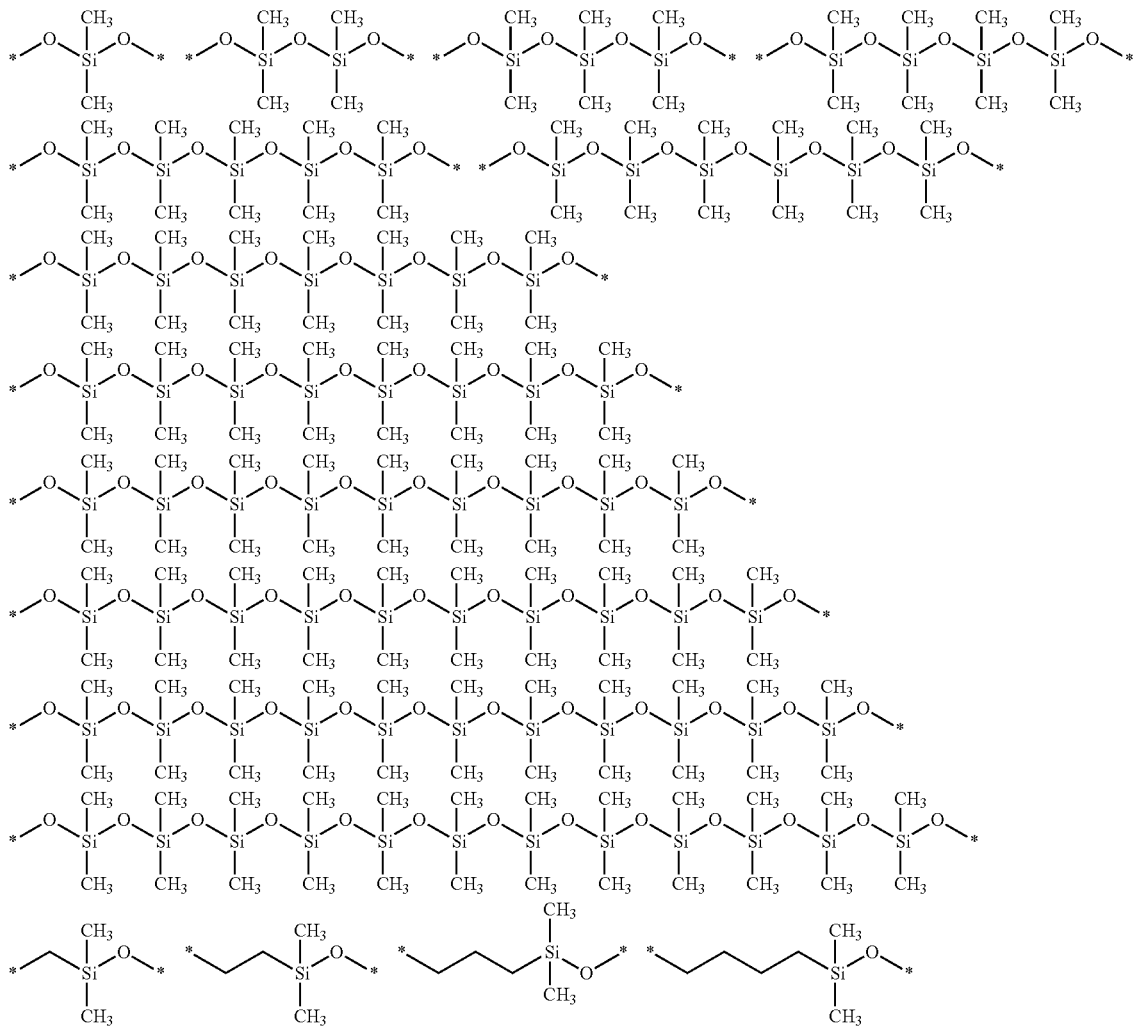

The number of elements forming the trialkylsilyl containing molecular chain is preferably not less than 24, more preferably not less than 40, further preferably not less than 50, and preferably not more than 1200, more preferably not more than 700, further preferably not more than 250.

Preferably, the trialkylsilyl containing molecular chain is represented by the following formula (s1).

$$*—R^{s2}—Si(R^{s1})_3 \qquad (s1)$$

wherein each of $R^{s1}$ independently represents a hydrocarbon group or a trialkylsilyloxy group, provided that these hydrocarbon groups are alkyl groups when all $R^{s1}$ are hydrocarbon groups;

$R^{s2}$ represents a dialkylsiloxane chain and an oxygen atom in the dialkylsiloxane chain may be replaced by a divalent hydrocarbon group and a part of methylene groups (—CH$_2$—) in the divalent hydrocarbon group may be replaced by oxygen atoms; and

* represents a bond with silicon atom.

In the formula (s1), the carbon number of the hydrocarbon group of $R^{s1}$ is preferably not less than 1 and not more than 4, more preferably not less than 1 and not more than 3, further preferably not less than 1 and not more than 2. The hydrocarbon group of $R^{s1}$ may be linear or branched, and preferably linear. The hydrocarbon group of $R^{s1}$ is preferably an aliphatic hydrocarbon group, more preferably an alkyl group. Specific examples of the hydrocarbon group of $R^{s1}$ include linear saturated aliphatic hydrocarbon groups such as methyl group, ethyl group, propyl group and butyl group.

The trialkylsilyloxy group of $R^{s1}$ can be appropriately selected from the groups described above. $R^{s1}$ is preferably an alkyl group when all of $R^{s1}$ are hydrocarbon groups.

The dialkylsiloxane chain of $R^{s2}$, and the divalent hydrocarbon group that may replace an oxygen atom in the dialkylsiloxane chain of $R^{s2}$ can be appropriately selected from the groups described above.

The trialkylsilyl containing chain is preferably represented by the formula (s1-1), more preferably represented by the formula (S1-1-1):

$$*—(O—Si(R^{s3})_2)_{n1}—(R^{s4})_{m1}—Si(O—Si(R^{s5})_3)_3 \qquad (s1-1)$$

wherein each of $R^{s3}$ independently represents an alkyl group with a carbon number of not less than 1 and not more than 4;

$R^{s4}$ represents a divalent hydrocarbon group with a carbon number of not less than 1 and not more than 10, and a methylene group (—CH$_2$—) in $R^{s4}$ may be replaced by an oxygen atom;

each of $R^{s5}$ independently represents an alkyl group with a carbon number of not less than 1 and not more than 4;

m1 and n1 independently represent an integer of not less than 0; and

* represents a bond with silicon atom;

provided that occurrence order of the repeating units parenthesized with the subscripts of n1 and m1 is arbitrary in the formula.

$$*—(O—Si(R^{s3})_2)_{n1}—Si(O—Si(R^{s5})_3)_3 \qquad (s1-1-1)$$

wherein $R^{s3}$, $R^{s5}$ and n1 respectively represent the same meaning as above, and

* represents a bond with silicon atom.

The trialkylsilyl containing chain is preferably represented by the formula (s1-2), more preferably represented by the formula (S1-2-1):

$$*—(O—Si(R^{s8})_2)_{n2}—(R^{s9})_{m2}—Si(R^{s10})_3 \qquad (s1-2)$$

wherein each of $R^{s8}$ independently represents an alkyl group with a carbon number of not less than 1 and not more than 4;

$R^{s9}$ represents a divalent hydrocarbon group with a carbon number of not less than 1 and not more than 10, and a methylene group (—CH$_2$—) in $R^{s9}$ may be replaced by an oxygen atom;

each of $R^{s10}$ independently represents an alkyl group with a carbon number of not less than 1 and not more than 4;

m2 and n2 independently represent an integer of not less than 0; and

* represents a bond with silicon atom;

provided that occurrence order of the repeating units parenthesized with the subscripts of n2 and m2 is arbitrary in the formula.

$$*—(O—Si(R^{s8})_2)_{n2}—Si(R^{s10})_3 \qquad (s1-2-1)$$

wherein $R^{s8}$, $R^{s10}$ and n2 respectively represent the same meaning as above, and

* represents a bond with silicon atom.

In the formulae (s1-1), (s1-1-1), (s1-2) and (s1-2-1), the carbon number of each of the alkyl groups of $R^{s3}$ and $R^{s8}$ is preferably not less than 1 and not more than 3, more preferably not less than 1 and not more than 2, especially preferably 1. Specific examples of the alkyl group of $R^{s3}$ include methyl group, ethyl group and propyl group.

The divalent hydrocarbon groups of $R^{s4}$ and $R^{s9}$ can be appropriately selected from the groups described above as hydrocarbon groups that may replace oxygen atoms in the dialkylsiloxane chain, and the divalent hydrocarbon groups are each preferably a linear or branched divalent saturated aliphatic hydrocarbon group with a carbon number of 1 to 4.

The alkyl groups of $R^{s5}$ and $R^{s10}$ can be appropriately selected from the groups described above as alkyl groups in the trialkylsilyl group, and the carbon number of the alkyl group included in the group *—Si(R$^{s5}$)$_3$ or *—Si(R$^{s10}$)$_3$ is preferably not less than 1 and not more than 4, more preferably not less than 1 and not more than 3, further preferably not less than 1 and not more than 2. The total carbon number of three alkyl groups included in the trialkylsilyl group is preferably not more than 9, more preferably not more than 6, further preferably not more than 4. Preferably, the group *—Si(R$^{s5}$)$_3$ includes at least one methyl group, more preferably two or more methyl groups. Especially preferably, all the three alkyl groups are methyl groups.

m1 and m2 are each preferably not less than 0 and not more than 4, more preferably not less than 0 and not more than 3. n1 and n2 are each preferably not less than 1 and not more than 100, more preferably not less than 1 and not more than 80, further preferably not less than 1 and not more than 50, especially preferably not less than 1 and not more than 30, most preferably not less than 1 and not more than 20.

It is to be noted that the occurrence order of the repeating units parenthesized with the subscripts of n1 and m1 is arbitrary in the formula.

The occurrence order of the repeating units parenthesized with the subscripts of n1 and m1, and the occurrence order of the repeating units parenthesized with the subscripts of n2 and m2 may be as described in the formula.

Specific examples of the trialkylsilyl containing molecular chain include groups represented by the following groups.

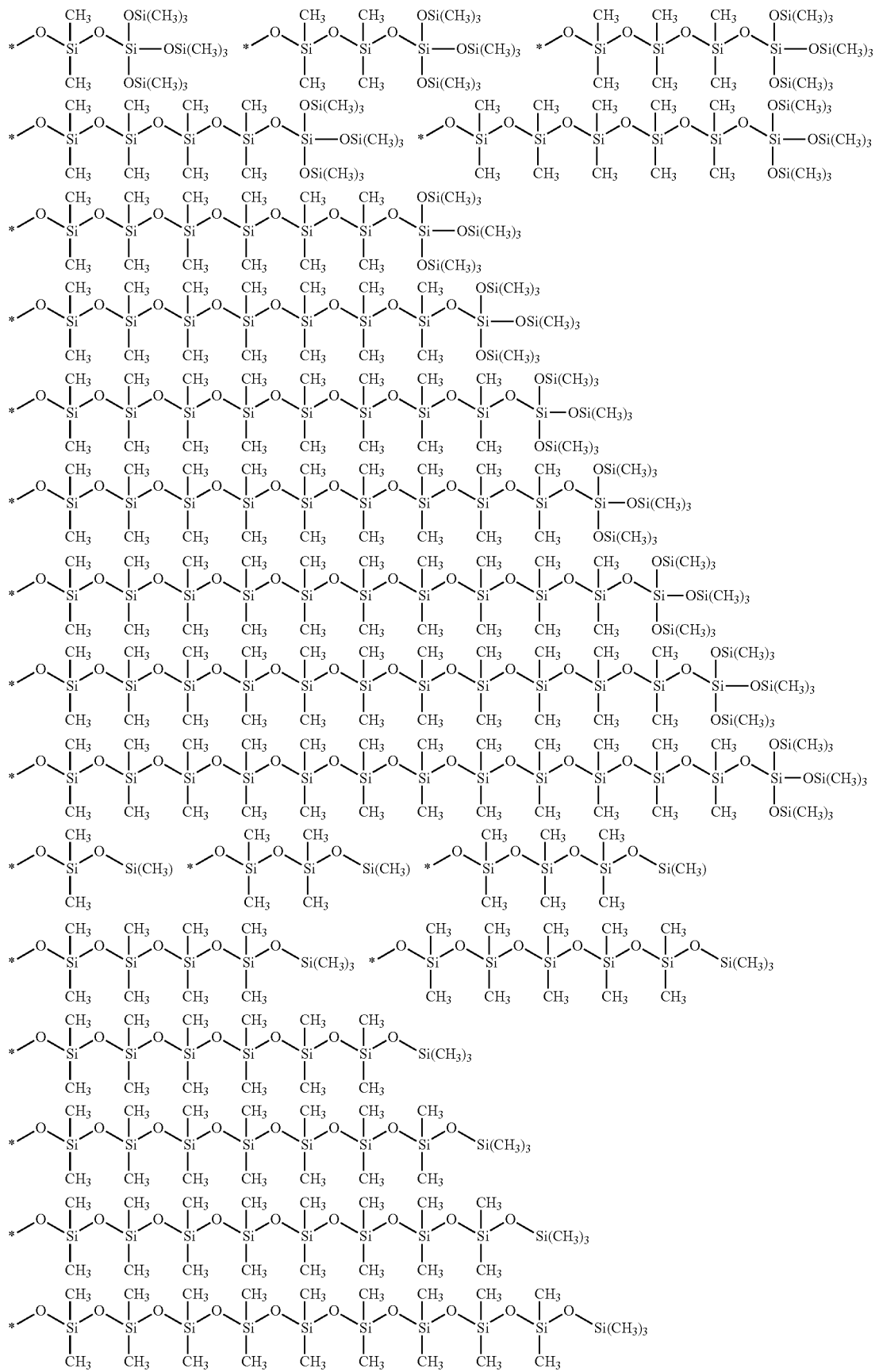

-continued

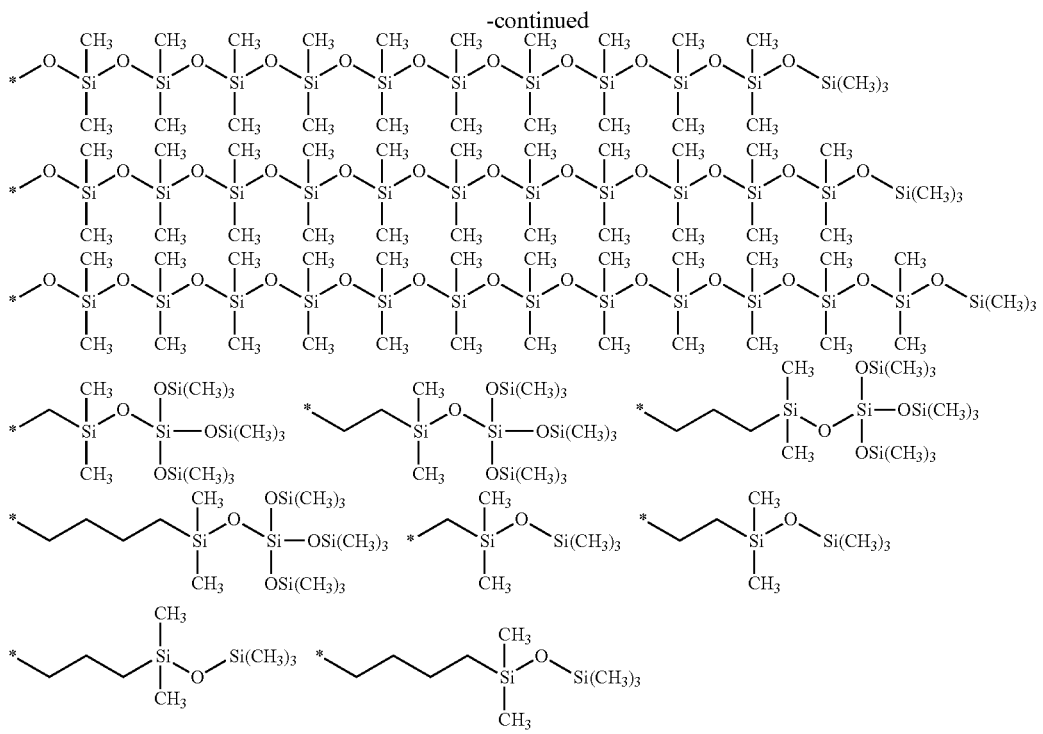

Two —O— groups for a siloxane bond are bonded to a silicon atom to which the trialkylsilyl containing molecular chain is bonded, and as the other one group, a siloxane containing group with an element number smaller than the number of elements forming the molecular chain in the trialkylsilyl containing molecular chain; or a group containing a hydrocarbon chain with a carbon number smaller than the number of elements forming the molecular chain in the trialkylsilyl containing molecular chain (hereinafter, the group is sometimes referred to as a "hydrocarbon chain-containing group); may be bonded to the silicon atom.

The siloxane containing group should be a group that contains a siloxane unit (Si—O—), and is formed by elements in a number smaller than the number of elements forming the molecular chain in the trialkylsilyl containing molecular chain. The siloxane containing group is thus a group that has a shorter length or a smaller three-dimensional size (bulkiness) as compared to the trialkylsilyl containing molecular chain.

The siloxane containing group is preferably in a chain form, and the chain may be linear or branched. In the siloxane containing group, the siloxane unit (Si—O—) is preferably a dialkylsilyloxy group. Examples of the dialkylsilyloxy group include dimethylsilyloxy group and diethylsilyloxy group. The number of the repeating siloxane units (Si—O—) is preferably not less than 1, and preferably not more than 5, more preferably not more than 3.

The siloxane containing group may include a divalent hydrocarbon group in a part of the siloxane backbone. Specifically, a part of oxygen atoms in the siloxane backbone may be replaced by divalent hydrocarbon groups. Preferred examples of the divalent hydrocarbon group that may replace a part of oxygen atoms in the siloxane backbone may include groups similar to the divalent hydrocarbon groups that may replace oxygen atoms in the dialkylsiloxane chain in the trialkylsilyl containing molecular chain.

The silicon atom at one end (free end) of the siloxane containing group may have a hydrocarbon group (preferably an alkyl group) or hydroxy group in addition to the —O— group for forming a siloxane unit (Si—O—) with the adjacent silicon atom etc. Here, the siloxane containing group comprises a trialkylsilyl group, and the siloxane containing group may exhibit a function as a spacer since the number of elements is smaller than the number of elements in the coexisting trialkylsilyl containing molecular chain. The alkyl groups in the trialkylsilyl group may be replaced by fluoroalkyl groups when the siloxane containing group includes a trialkylsilyl group.

The number of elements in the siloxane containing group is preferably not more than 100, more preferably not more than 50, further preferably not more than 30, and is normally not less than 10. The difference in the number of elements between the trialkylsilyl containing molecular chain and the siloxane containing group is preferably not less than 10, more preferably not less than 20, and is normally, preferably not more than 1000, more preferably not more than 500, further preferably not more than 200.

For example, the siloxane containing group is preferably a group represented by the following formula (s2).

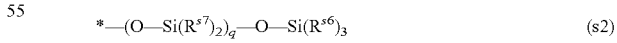

(s2)

wherein each of $R^{s6}$ independently represents a hydrocarbon group or hydroxy group;

each of $R^{s7}$ independently represents an alkyl group with a carbon number of not less than 1 and not more than 4;

q represents an integer of not less than 0 and not more than 4; and

* represents a bond with silicon atom.

Examples of the hydrocarbon group of $R^{s6}$ in the formula (s2) include groups similar to the groups shown as examples of the hydrocarbon group of $R^{s1}$. The hydrocarbon group of $R^{s6}$ is preferably an aliphatic hydrocarbon group, and more preferably a linear saturated aliphatic hydrocarbon group such as methyl group, ethyl group, propyl group or butyl group.

$R^{s6}$ is preferably a hydrocarbon group. The methylene group included in the hydrocarbon group of $R^{s6}$ may be replaced by an oxygen atom.

Examples of the alkyl group of $R^{s7}$ with a carbon number of not less than 1 and not more than 4 in the formula (s2) include groups similar to the groups described as $R^{s3}$ in the formula (s1-1).

Specific examples of the siloxane containing group include groups represented by the following formulae.

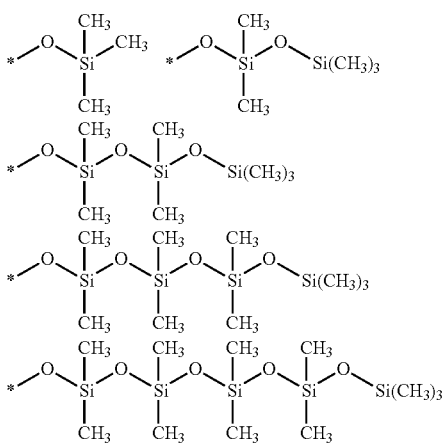

The hydrocarbon chain-containing group should have a hydrocarbon chain moiety with a carbon number that is smaller than the number of elements forming the molecular chain in the trialkylsilyl containing molecular chain. The carbon number of the longest linear chain in the hydrocarbon chain is preferably smaller than the number of elements forming the longest linear chain in the trialkylsilyl containing molecular chain. The hydrocarbon chain-containing group is normally composed only of a hydrocarbon group (hydrocarbon chain), but may be a group in which some of methylene groups (—CH$_2$—) of the hydrocarbon chain are replaced by oxygen atoms. Methylene groups (—CH$_2$—) adjacent to Si atoms are not replaced by oxygen atoms, and two continuous methylene groups (—CH$_2$—) are not simultaneously replaced by oxygen atoms.

The carbon number of the hydrocarbon chain moiety means the number of carbon atoms that form the hydrocarbon group (hydrocarbon chain) in the case of an oxygen-unsubstituted hydrocarbon chain-containing group, while the carbon number of the hydrocarbon chain moiety means the number of carbon atoms, which is counted with the assumption that oxygen atoms are considered as methylene groups (—CH$_2$—), in the case of an oxygen-substituted hydrocarbon chain-containing group.

Hereinafter, the hydrocarbon chain-containing group is described and an oxygen-unsubstituted hydrocarbon chain-containing group (i.e., monovalent hydrocarbon group) is taken as an example unless otherwise specified, and a part of the methylene groups (—CH$_2$—) can be replaced by oxygen atoms in the following.

The carbon number of the hydrocarbon chain-containing group is preferably not less than 1 and not more than 3, more preferably 1 when the hydrocarbon chain-containing group is a hydrocarbon group. The hydrocarbon chain-containing group (in the case of a hydrocarbon group) may be a branched chain or a linear chain. The hydrocarbon chain-containing group (in the case of a hydrocarbon group) is preferably a saturated or unsaturated aliphatic hydrocarbon chain-containing group, more preferably a saturated aliphatic hydrocarbon chain-containing group. The saturated aliphatic hydrocarbon chain-containing group (in the case of a hydrocarbon group) is more preferably a saturated aliphatic hydrocarbon group. Examples of the saturated aliphatic hydrocarbon group include methyl group, ethyl group and propyl group.

When a part of methylene groups (—CH$_2$—) of a saturated aliphatic hydrocarbon group are replaced by oxygen atoms, specific examples may include groups having (poly) ethylene glycol units.

Preferably, the structure (A) in which the trialkylsilyl containing molecular chain is bonded to a silicon atom that forms the polysiloxane backbone is represented by the following formula (1) for example.

wherein $R^a$ represents a trialkylsilyl containing molecular chain;

$Z^{a1}$ represents a trialkylsilyl containing molecular chain, a siloxane containing group, a hydroparbon chain containing group or —O— group, and $R^a$ and $Z^{a1}$ may be the same or different when $Z^{a1}$ represents a trialkylsilyl containing molecular chain, and $R^a$ and $Z^{a1}$ may be the same or different among a plurality of formulae (I).

In the formula (1), the trialkylsilyl containing molecular chain of $R^a$ or $Z^{a1}$, the siloxane containing group of $Z^{a1}$ and the hydrocarbon chain-containing group can be appropriately selected from the groups described above as the trialkylsilyl containing molecular chain, the siloxane containing group and the hydrocarbon chain-containing group, respectively.

In particular, in the formula (1), $Z^{a1}$ is preferably a siloxane containing group or —O— group, and more preferably —O— group.

Preferred examples of the structure (A) may include structures represented by the following formulae (1-1) to (1-32).

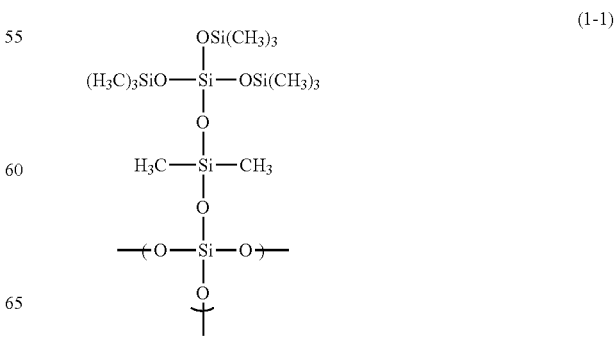

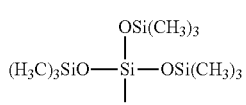
(1-2)
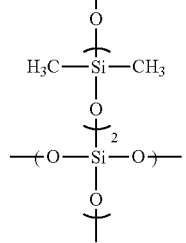
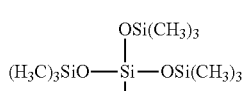
(1-3)
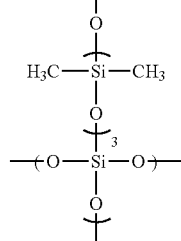
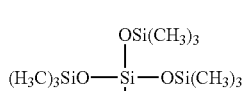
(1-4)
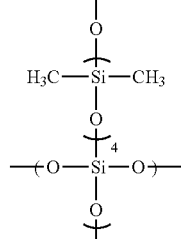
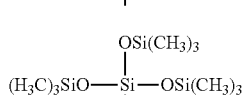
(1-5)
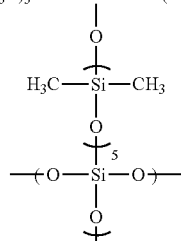
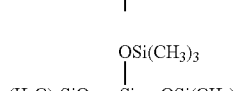
(1-6)
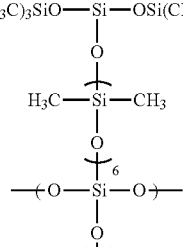
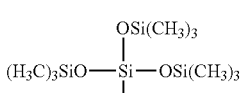
(1-7)
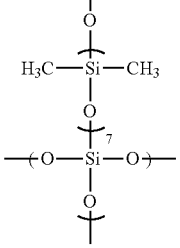
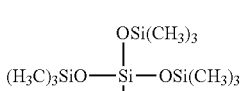
(1-8)
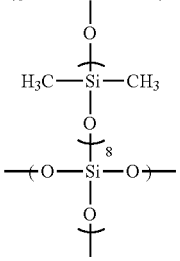
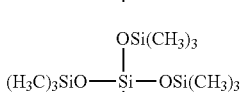
(1-9)
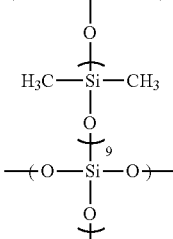
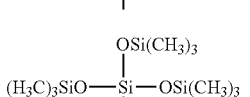
(1-10)
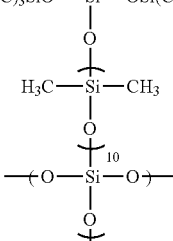
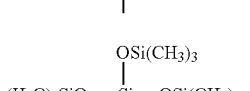
(1-11)
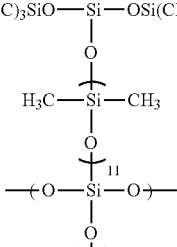

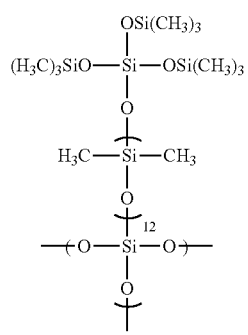 (1-12)
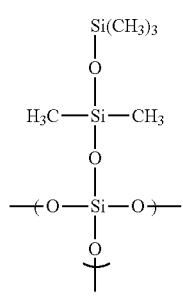 (1-13)
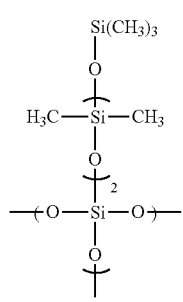 (1-14)
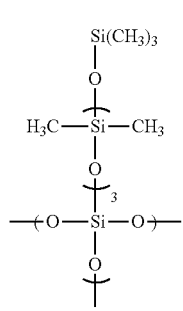 (1-15)
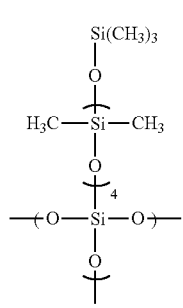 (1-16)
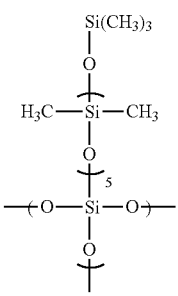 (1-17)
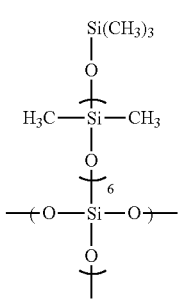 (1-18)
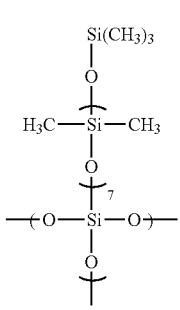 (1-19)
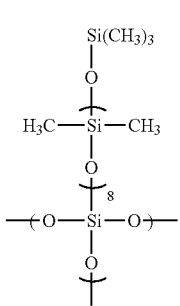 (1-20)
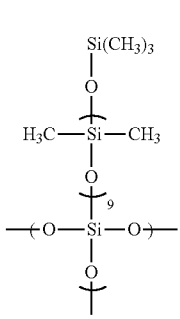 (1-21)

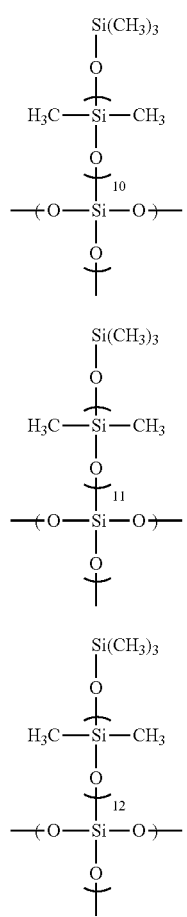
(1-22)
(1-23)
(1-24)
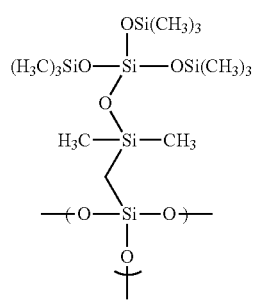
(1-25)
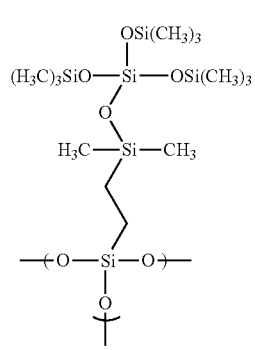
(1-26)
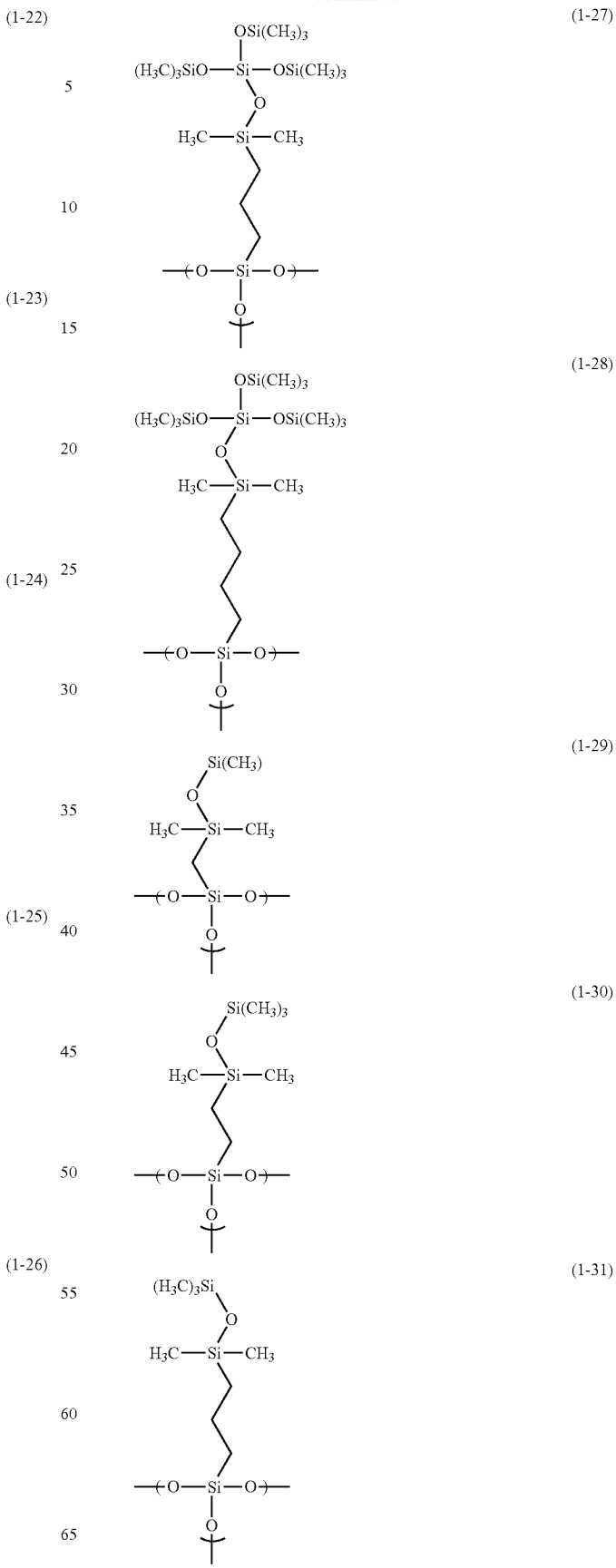
(1-27)
(1-28)
(1-29)
(1-30)
(1-31)

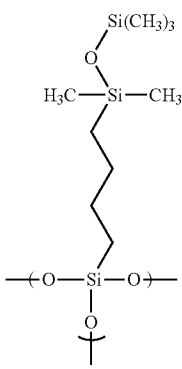
(1-32)

The transparent film of the present invention may further comprise a structure (B) where a unit that includes a metal atom and a group bonded to the metal atom selected from the siloxane containing group, the hydrocarbon chain-containing group and hydroxy group, wherein the metal atom is selected from trivalent and tetravalent metal atoms that is capable of forming a metal alkoxide, the number of elements in the siloxane containing group is smaller than the number of elements in the molecular chain of the trialkylsilyl containing molecular chain, and the structure (B) is bonded to the polysiloxane backbone at the position of the metal atom. Particularly, when the above-mentioned siloxane containing group, hydrocarbon chain-containing group or hydroxy group is bonded to a silicon atom (second silicon atom) or a metal atom that is different from the silicon atom to which the trialkylsilyl containing molecular chain is bonded, the second silicon atom or the metal atom also acts as a spacer since a hydrocarbon chain-containing group with a small carbon number or hydroxy group is bonded, and thus the function of improving the water/oil repellency characteristic by the trialkylsilyl containing molecular chain can be improved. The group bonded to the metal atom is preferably a siloxane containing group or hydroxy group.

The structure (B) in which the hydrocarbon chain-containing group is bonded to the second silicon atom or other metal atom is preferably a structure represented by any one of the following formulae (2-I) to (2-III), more preferably a structure represented by the formula (2-I).

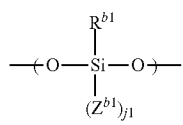
(2-I)

wherein $R^{b1}$ represents the siloxane containing group, the hydrocarbon containing-group, hydroxy group or —O— group;
$Z^{b1}$ represents the siloxane containing group, the hydrocarbon containing-group, hydroxy group or —O— group, $R^{b1}$ and $Z^{b1}$ may be the same or different when $Z^{b1}$ and $R^{b1}$ represent siloxane containing groups or hydrocarbon containing-groups, $R^{b1}$ and $Z^{b1}$ may be the same or different among a plurality of formulae (2-I);
M represents the trivalent or tetravalent metal atom capable of forming the metal alkoxide; and
j represents an integer of 0 or 1 depending on M.

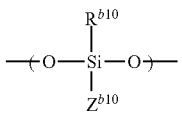
(2-II)

wherein $R^{b10}$ represents a fluorine-containing alkyl group;
$Z^{b10}$ represents the siloxane containing group, the hydrocarbon chain-containing group, the hydrolyzable group or —O— group, and $R^{b10}$ and $Z^{b10}$ may be the same or different among a plurality of formulae (2-II).

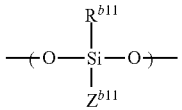
(2-III)

wherein $R^{b11}$ represents a hydrolyzable silane oligomer residue;
$Z^{b11}$ represents a hydrolyzable group, a fluorine-containing alkyl group with a carbon number of 1 to 12, an alkyl group with a carbon number of 1 to 4 or —O— group.

In the formula (2-I), the siloxane containing group and hydrocarbon chain-containing group of $R^{b1}$ and $Z^{b1}$ can be appropriately selected from the groups described above.

In particular, $R^{b1}$ is preferably a siloxane containing group, a hydrocarbon chain-containing group or hydroxy group, more preferably a siloxane containing group or hydroxy group, still more preferably hydroxy group. $R^{b1}$ is preferably —O— group.

$Z^{b1}$ is preferably a siloxane containing group, hydroxy group or —O— group, more preferably hydroxy group or —O— group.

Examples of the metal M include trivalent metals such as B, Al, Ge, Ga, Y, In, Sb and La; and tetravalent metals such as Si, Ti, Ge, Zr, Sn and Hf, and Al, Si, Ti and Zr are preferred, with Si being especially preferred.

In the formula (2-I), j1 represents 0 when M is a trivalent metal, and j1 represents 1 when M is a tetravalent metal.

In the formula (2-II), the fluorine-containing alkyl group represented by $R^{b10}$ is preferably a group with a carbon number of 1 to 15, more preferably a group with a carbon number of 1 to 12, further preferably a group with a carbon number of 1 to 8, especially preferably a group with a carbon number of 1 to 6. Specifically, a group having a fluoroalkyl group at one end is preferred, and particularly, a group having a trifluoromethyl group at one end is preferred. The fluorine-containing alkyl group is preferably a group represented by the formula (f-1).

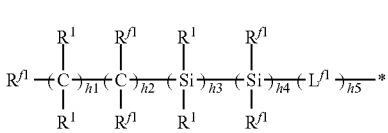
(f-1)

wherein each of $R^{f1}$ independently represents a fluorine atom, or an alkyl group substituted with one or more fluorine atoms with a carbon number of 1 to 12;
each of $R^1$ independently represents hydrogen atom or an alkyl group with a carbon number of 1 to 4;

each of $L^{f1}$ independently represents —O—, —COO—, —OCO—, —NR—, —NRCO— or —CONR— (R represents hydrogen atom, an alkyl group with a carbon number of 1 to 4, or a fluorine-containing alkyl group with a carbon number of 1 to 4);

h1 to h5 each independently represent an integer of not less than 0 and not more than 100, and the total value of h1 to h5 is not more than 100;

the order of the repeating units parenthesized with the subscripts of h1 to h5 and is arbitrary in the formula; and

* represents a bond with M.

It is to be noted that in the formula (f-1), repeating units including Si are not mutually adjacent.

$R^{f1}$ is preferably fluorine atom, or a perfluoroalkyl with a carbon number of 1 to 10 (more preferably with a carbon number of 1 to 5). $R^1$ is preferably hydrogen atom or an alkyl with a carbon number of 1 to 4. A is preferably —O—, —COO— or —OCO—. h1 is preferably not less than 1 and not more than 30, more preferably not less than 1 and not more than 25, further preferably not less than 1 and not more than 10, especially preferably not less than 1 and not more than 5, most preferably 1 or 2. h2 is preferably not less than 0 and not more than 15, more preferably not less than 0 and not more than 10. h3 is preferably not less than 0 and not more than 5, more preferably not less than 0 and not more than 2. h4 is preferably not less than 0 and not more than 4, more preferably not less than 0 and not more than 2. h5 is preferably not less than 0 and not more than 4, more preferably not less than 0 and not more than 2. The total value of h1 to h5 is preferably not less than 3, more preferably not less than 5, and preferably not more than 80, more preferably not more than 50, further preferably not more than 20.

Particularly, it is preferred that $R^{f1}$ is fluorine atom or a perfluoroalkyl with a carbon number of 1 to 5, $R^1$ is hydrogen atom, each of h3, h4 and h5 is 0, h1 is not less than 1 and not more than 5, and h2 is not less than 0 and 5.

Examples of the fluorine-containing alkyl group include $C_{r1}F_{2r1+1}$— (r1 is an integer of 1 to 12), $CF_3CH_2O(CH_2)_{r2}$—, $CF_3(CH_2)_{r3}Si(CH_3)_2(CH_2)_{r2}$—, $CF_3COO(CH_2)_{r2}$— (r2 is 5 to 20, preferably 8 to 15, and r3 is 1 to 7, preferably 2 to 6), $CF_3(CF_2)_{r4}$—$(CH_2)_{r5}$— and $CF_3(CF_2)_{r4}$—$C_6H_4$— (r4 is 1 to 10, preferably 3 to 7, and r5 is 1 to 5, preferably 2 to 4).

Examples of the fluorine-containing alkyl group include fluoroalkyl groups, fluoroalkyloxyalkyl groups, fluoroalkylsilylalkyl groups, fluoroalkylcarbonyloxyalkyl groups, fluoroalkylaryl groups, fluoroalkylalkenyl groups and fluoroalkylalkynyl groups.

Examples of the fluoroalkyl group include fluoroalkyl groups with a carbon number of 1 to 12, such as fluoromethyl group, fluoroethyl group, fluoropropyl group, fluorobutyl group, fluoropentyl group, fluorohexyl group, fluoroheptyl group, fluorooctyl group, fluorononyl group, fluorodecyl group, fluoroundecyl group and fluorododecyl group.

Examples of the fluoroalkoxyalkyl group include fluoromethoxy $C_{5-20}$ alkyl groups, fluoroethoxy $C_{5-20}$ alkyl groups, fluoropropoxy $C_{5-20}$ alkyl groups and fluorobutoxy $C_{5-20}$ alkyl groups.

Examples of the fluoroalkylsilylalkyl group include fluoromethylsilyl $C_{5-20}$ alkyl groups, fluoroethylsilyl $C_{5-20}$ alkyl groups, fluoropropylsilyl $C_{5-20}$ alkyl groups, fluorobutylsilyl $C_{5-20}$ alkyl groups, fluoropentylsilyl $C_{5-20}$ alkyl groups, fluorohexylsilyl $C_{5-20}$ alkyl groups, fluoroheptylsilyl $C_{5-20}$ alkyl groups and fluorooctylsilyl $C_{5-20}$ alkyl groups.

Examples of the fluoroalkylcarbonyloxyalkyl group include fluoromethylcarbonyloxy $C_{5-20}$ alkyl groups, fluoroethylcarbonyloxy $C_{5-20}$ alkyl groups, fluoropropylcarbonyloxy $C_{5-20}$ alkyl groups and fluorobutylcarbonyloxy $C_{5-20}$ alkyl groups.

Examples of the fluoroalkylaryl group include fluoro $C_{1-8}$ alkylphenyl groups and fluoro $C_{1-8}$ alkylnaphthyl groups. Examples of the fluoroalkylalkenyl group include fluoro $C_{1-17}$ alkylvinyl groups. Examples of fluoroalkylalkynyl group include fluoro $C_{1-17}$ alkylethynyl groups.

$Z^{b10}$ is preferably a siloxane containing group, hydroxy group or —O— group, more preferably hydroxy group or —O— group.

In the formula (2-III), the number of silicon atoms contained in the hydrolyzable silane oligomer residue of $R^{b11}$ is, for example, not less than 3, preferably not less than 5, more preferably not less than 7. The condensation number is preferably not more than 15, more preferably not more than 13, further preferably not more than 10.

When the oligomer residue comprises an alkoxy group, examples of the alkoxy group include methoxy group, ethoxy group, propoxy group and butoxy group, and methoxy group, ethoxy group and the like are preferred. The oligomer residue may comprise one or more of these alkoxy groups. Preferably, the oligomer residue comprises one alkoxy group.

The hydrolyzable silane oligomer residue is preferably a group represented by the following formula (f-2).

(f-2)

wherein X represents a hydrolyzable group, a fluorine-containing alkyl group with a carbon number of 1 to 12, or an alkyl group with a carbon number of 1 to 4;

h6 is an integer of not less than 0 and not more than 100, and

* represents a bond with Si.

In the formula (f-2), the hydrolyzable group of X is preferably an alkoxy group with a carbon number of 1 to 4 (preferably 1 or 2), such as methoxy group, ethoxy group, propoxy group or butoxy group; or allyl group. h6 is preferably not less than 0 and not more than 10, more preferably not less than 0 and not more than 7. Preferably, at least one of X is a fluorine-containing alkyl group with a carbon number of 1 to 12 (preferably with a carbon number of 1 to 4). Preferably, at least one of X is a hydrolyzable group (particularly, methoxy group, and ethoxy group or allyl group).

X is preferably a hydrolyzable group, or a fluorine-containing alkyl group with a carbon number of 1 to 12 (preferably with a carbon number of 1 to 4).

Examples of the hydrolyzable silane oligomer residue of $R^{b11}$ include $(C_2H_5O)_3Si$—$(OSi(OC_2H_5)_2)_4O$—* and $(CH_3O)_2(CF_3CH_2CH_2)Si$—$(OSi(OCH_3)(CH_2CH_2CF_3))_4$—O—*.

Examples of the hydrolyzable group in $Z^{b11}$ in the formula (2-III) include alkoxy groups with a carbon number of 1 to 4 (preferably 1 or 2), such as methoxy group, ethoxy group, propoxy group and butoxy group; hydrogen atom; cyano group; and allyl group, and alkoxy groups are preferred.

$Z^{b11}$ is preferably a hydrolyzable group, a fluorine-containing alkyl group with a carbon number of 1 to 12, or an —O— group.

The carbon number of the fluorine-containing alkyl group in $Z^{b11}$ is preferably 1 to 8, more preferably 1 to 4. The fluorine-containing alkyl group refers to a group in which a part or all of hydrogen atoms contained in an alkyl group such as methyl group, ethyl group, propyl group or butyl group are replaced by fluorine atoms. Examples of the fluorine-containing alkyl group include fluoroalkyl groups such as fluoromethyl group, fluoroethyl group, fluoropropyl group and fluorobutyl group; and perfluoroalkyl groups such as perfluoromethyl group, perfluoroethyl group, perfluoropropyl group and perfluorobutyl group.

The carbon number of the alkyl group in $R^{b11}$ is preferably 1 to 3, more preferably 1 or 2. Examples of the alkyl group in $R^{b11}$ include methyl group, ethyl group, propyl group and butyl group.

Preferred examples of the structure (B) may include structures represented by the following formulae (2-1) to (2-5) when M is Si.

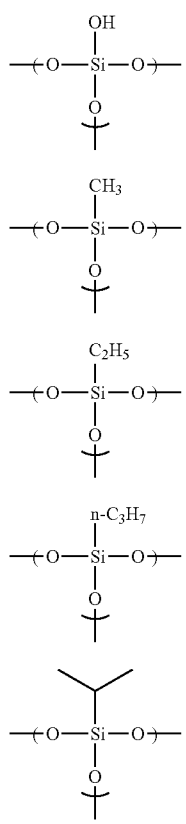

In the transparent film of the present invention, the abundance ratio of the structure (B) to the structure as (A) structure (B)/structure (A) is preferably not less than 0.1, more preferably not less than 5, further preferably not less than 8, and preferably not more than 80, more preferably not more than 60, further preferably not more than 50 in terms of moles.

The transparent film of the present invention attains water/oil repellency as well as heat resistance and light resistance because a change in contact angle before and after thermal history or before and after photoirradiation is controlled to a specific range. For securing the above-mentioned feature, it is preferred that the transparent film comprises a structure in which the trialkylsilyl containing molecular chain is bonded to a part of silicon atoms on the polysiloxane backbone that forms the transparent film. For forming such a transparent film, the following procedure should be carried out: an organosilicon compound (a) in which at least one trialkylsilyl containing molecular chain and at least one hydrolyzable group are bonded to a silicon atom; and a metal compound (b) in which a hydrolyzable group is bonded to a metal atom; are mixed, next the mixture is diluted with a solvent (c) as necessary to prepare a coating composition containing the organosilicon compound (a), the metal compound (b) and the optional solvent (c), and the coating composition is brought into contact with a substrate in air. By contacting the coating composition with the substrate in air, the hydrolyzable groups of the organosilicon compound (a) and the metal compound (b) are subjected to hydrolysis and polycondensation to form a siloxane backbone with a trialkylsilyl containing molecular chain bonded to silicon atoms on the backbone.

The organosilicon compound (a) is preferably an organosilicon compound in which at least one trialkylsilyl containing molecular chain and at least one hydrolyzable group are bonded to a silicon atom in one molecule.

In the organosilicon compound (a), the number of the trialkylsilyl containing molecular chains bonded to the center silicon atom is preferably not less than 1 and not more than 3, more preferably not more than 2, especially preferably 1.

The hydrolyzable group should be a group that gives hydroxy group (silanol group) through hydrolysis, and preferred examples thereof may include alkoxy groups with a carbon number of 1 to 4, such as methoxy group, ethoxy group, propoxy group and butoxy group; hydroxy group; acetoxy group; chlorine atom; and isocyanate group. In particular, alkoxy groups with a carbon number of 1 to 4 are preferred, and alkoxy groups with a carbon number of 1 or 2 are more preferred.

In the organosilicon compound (a), the number of the hydrolyzable groups bonded to the center silicon atom is not less than 1, preferably not less than 2, and is normally preferably not more than 3.

In addition to the trialkylsilyl containing molecular chain and the hydrolyzable group, a siloxane containing group with an element number smaller than the number of elements forming the molecular chain in the trialkylsilyl containing molecular chain, or a hydrocarbon chain-containing group containing a hydrocarbon chain with a carbon number smaller than the number of elements forming the molecular chain in the trialkylsilyl containing molecular chain may be bonded to the center silicon atom in the organosilicon compound (a).

Specifically, the organosilicon compound (a) is preferably a compound represented by the following formula (I).

wherein $R^a$ represents a trialkylsilyl containing molecular chain;

each of $A^{a1}$ independently represents a hydrolyzable group;

$Z^{a2}$ represents a trialkylsilyl containing molecular chain, a hydrocarbon chain-containing group, a siloxane containing group or a hydrolysable group, $Z^{a2}$ and $A^{a1}$ may be the same or different when $Z^{a2}$ represents the hydrolysable group, and $R^a$ and $Z^{a2}$ may be the same or different among plurality of formulae (I)

In the formula (I), the trialkylsilyl containing molecular chain of $R^a$ or $Z^{a2}$, the hydrocarbon chain-containing group of $Z^{a2}$, the siloxane containing group of $Z^{a2}$ and the hydrolyzable group of $A^{a1}$ or $Z^{a2}$ can be appropriately selected from the groups described above as the trialkylsilyl containing molecular chain, the hydrocarbon chain-containing group, the siloxane containing group and the hydrolyzable group, respectively.

In the formula (I), $Z^{a2}$ is preferably a siloxane containing group or a hydrolyzable group, more preferably a hydrolyzable group. When $Z^{a2}$ is a hydrolyzable group, $Z^{a2}$ and $A^{a1}$ are preferably the same.

In particular, the organosilicon compound (a) is preferably a compound represented by the following formula (I-I).

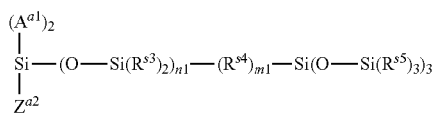
(I-I)

wherein each of $A^{a1}$ independently represents the hydrolyzable group;

$Z^{a2}$ represents a trialkylsilyl containing molecular chain, a hydrocarbon chain-containing group, a siloxane containing group or a hydrolyzable group, and $Z^{a2}$ and $A^{a1}$ may be the same or different when $Z^{a2}$ represents a hydrolyzable group, and $R^a$ and $Z^{a2}$ may be the same or different among a plurality of formulae (I-I);

each of $R^{a2}$ independently represents an alkyl group with a carbon number of not less than 1 and not more than 4;

$R^{s4}$ represents a divalent hydrocarbon group with a carbon number of not less than 1 and not more than 10, and a methylene group (—CH$_2$—) in $R^{s4}$ may be replaced by an oxygen atom;

each of $R^{s5}$ independently represents an alkyl group with a carbon number of not less than 1 and not more than 4; and m1 and n1 independently represent an integer of not less than 0;

provided that occurrence order of the repeating units parenthesized with the subscripts n1 and m1 is arbitrary in the formula.

The organosilicon compound (a) is more preferably a compound represented by the following formula (I-I-1).

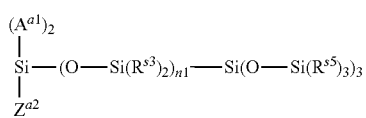
(I-I-1)

wherein $A^{a1}$, $Z^{a2}$, $R^{s3}$, $R^{s5}$ and n1 respectively represent the same meaning as above.

The organosilicon compound (a) is preferably a compound represented by the following formula (I-II).

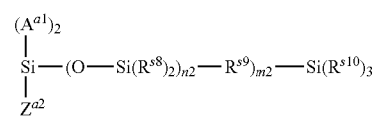
(I-II)

wherein each of $A^{a1}$ independently represents the hydrolyzable group;

$Z^{a2}$ represents a trialkylsilyl containing molecular chain, a hydrocarbon chain-containing group, a siloxane containing group or a hydrolyzable group, and $Z^{a2}$ and $A^{a1}$ may be the same or different when $Z^{a2}$ represents a hydrolyzable group, and $R^a$ and $Z^{a2}$ may be the same or different among a plurality of formulae (I-II);

each of $R^{s8}$ independently represents an alkyl group with a carbon number of not less than 1 and not more than 4;

$R^{s9}$ represents a divalent hydrocarbon group with a carbon number of not less than 1 and not more than 10, and a methylene group (—CH$_2$—) in $R^{s9}$ may be replaced by an oxygen atom;

each of $R^{s10}$ independently represents an alkyl group with a carbon number of not less than 1 and not more than 4; and m2 and n2 independently represent an integer of not less than 0;

provided that occurrence order of the repeating units parenthesized with the subscripts n2 and m2 is arbitrary in the formula.

Among the compound represented by the formula (I-II), the compound represented by the formula (I-II-1) is also preferable.

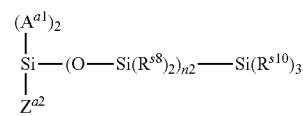
(I-II-1)

$A^{a1}$, $Z^{a2}$, $R^{s8}$, $R^{s10}$ and n2 respectively represent the same meaning as above.

The occurrence order of the repeating units parenthesized with the subscripts of n1 and m1 and, and the occurrence order of the repeating units parenthesized with the subscripts of n2 and m2 and may be as described in the formula.

Examples of the organosilicon compound (a) may include compounds having one trialkylsilyl containing molecular chain and three hydrolyzable groups; compounds having one trialkylsilyl containing molecular chain, one siloxane containing group and two hydrolyzable groups; and compounds having one trialkylsilyl containing molecular chain, one hydrocarbon chain-containing group and two hydrolyzable groups.

In the compound having one trialkylsilyl containing molecular chain and three hydrolyzable groups, the three hydrolyzable groups are bonded to a silicon atom. Examples of the group in which three hydrolyzable groups are bonded to a silicon atom include trialkoxysilyl groups such as trimethoxysilyl group, triethoxysilyl group, tripropoxysilyl group and tributoxysilyl group; trihydroxysilyl group; triacetoxysilyl group; trichlorosilyl group; and triisocyanatesilyl group, and examples of the compound having one trialkylsilyl containing molecular chain and three hydrolyzable groups include compounds in which one trialkylsilyl containing molecular chain selected from the groups described above is bonded to a silicon atom of the above-mentioned group in which three hydrolyzable groups are bonded to a silicon atom.

In the compound having one trialkylsilyl containing molecular chain, one siloxane containing group and two hydrolyzable groups, one siloxane containing group and two hydrolyzable groups are bonded to a silicon atom. Examples of the group in which one siloxane containing group and two hydrolyzable groups are bonded to a silicon atom include trimethylsilyloxydialkoxysilyl groups such as trimethylsilyloxydimethoxysilyl group, trimethylsilyloxydiethoxysilyl group and trimethylsilyloxydipropoxysilyl group, and examples of the compound having one trialkylsilyl containing molecular chain, one siloxane containing group and two hydrolyzable groups include compounds in which one trialkylsilyl containing molecular chain selected from the groups described above is bonded to a silicon atom at one end of the above-mentioned group in which one siloxane containing group and two hydrolyzable groups are bonded to a silicon atom.

In the compound having one trialkylsilyl containing molecular chain, one hydrocarbon chain-containing group and two hydrolyzable groups, one hydrocarbon chain-containing group and two hydrolyzable groups are bonded to a silicon atom. Examples of the group in which one hydrocarbon chain-containing group and two hydrolyzable groups are bonded to a silicon atom include alkyldialkoxysilyl groups such as methyldimethoxysilyl group, ethyldimethoxysilyl group, methyldiethoxysilyl group, ethyldiethoxysilyl group and methyldipropoxysilyl group, and examples of the compound having one trialkylsilyl containing molecular chain, one hydrocarbon chain-containing group and two hydrolyzable groups include compounds in which one trialkylsilyl containing molecular chain selected from the groups described above is bonded to a silicon atom of the above-mentioned group in which one hydrocarbon chain-containing group and two hydrolyzable groups are bonded to a silicon atom.

Examples of the method for synthesizing the organosilicon compound (a) include the following methods. As a first method, the organosilicon compound (a) can be produced by the reaction of a compound in which a trialkylsilyl containing molecular chain and a halogen atom (preferably a chlorine atom) are bonded to each other, with a compound in which three or more (particularly four) hydrolyzable groups are bonded to a silicon atom.

Among the organosilicon compounds (a), preferable is a compound having a group in which all alkyl groups of a trialkylsilyl group are replaced by trialkylsilyl groups as a trialkylsilyl containing molecular chain, which group is bonded to a dialkylsiloxane chain (a group in which m is 0 in the formula (s1-1)). This compound is a novel compound.

As a second synthesis method, the organosilicon compound (a) can be produced by the reaction of a compound in which a halogen atom is bonded to both ends of a dialkylsiloxane chain (hereinafter, referred to as a "dihalogenated dialkylsiloxane"), a compound in which tris(trialkylsilyloxy)silyl group and an $M^1O$— group ($M^1$ represents an alkali metal) are bonded to each other (hereinafter, referred to as an "alkali metal silyl oxide"), and a compound in which four hydrolyzable groups are bonded to a silicon atom. The reaction order of these compounds is not limited, and it is preferred to first react the dihalogenated dialkylsiloxane and the alkali metal silyl oxide, and then to react with the compound in which four hydrolyzable groups are bonded to a silicon atom.

Examples of the halogen atom include fluorine atom, chlorine atom, bromine atom and iodine atom, and chlorine atom is preferred. The alkali metal is preferably lithium.

The alkali metal silyl oxide can be produced by reacting an alkyl alkali metal with a compound in which tris(trialkylsilyloxy)silyl group and hydroxy group are bonded to each other for example. Examples of the organic alkali metal compound include alkyllithiums such as n-butyllithium, sec-butyllithium and tert-butyllithium, and n-butyllithium is especially preferred.

As a third synthesis method, the organosilicon compound can be produced by reacting an alkali metal silyl oxide and a cyclic dimethylsiloxane, and then reacting the product with a compound in which three hydrolyzable groups and one halogen atom (particularly chlorine atom) are bonded to a silicon atom for example. The number of silicon atoms contained in the cyclic dimethylsiloxane is preferably not less than 2 and not more than 10, more preferably not less than 2 and not more than 5, further preferably not less than 2 and not more than 4 for example.

The metal compound (b) is a metal compound in which at least one hydrolyzable group is bonded to the center metal atom. The siloxane containing group or the hydrocarbon chain-containing group may be bonded to the metal atom. Since the number of elements in the siloxane containing group, and the carbon number of the hydrocarbon chain moiety in the hydrocarbon chain-containing group are each smaller than the number of elements that form the molecular chain in the trialkylsilyl containing molecular chain bonded to the center silicon atom in the organosilicon compound (a), a part having a spacer function can be formed in the transparent film. The group bonded to the metal atom is preferably a siloxane containing group.

The center metal atom in the metal compound (b) should be a metal atom that is capable of forming a metal alkoxide with a bond to an alkoxy group, and the metals here include semimetals such as Si and Ge.

Specific examples of the center metal atom in the metal compound (b) include trivalent metals such as Al, Fe and In; tetravalent metals such as Hf, Si, Ti, Sn and Zr; and pentavalent metals such as Ta. Trivalent metals and tetravalent metals are preferred, and trivalent metals such as Al, Fe and In; and tetravalent metals such as Hf, Si, Ti, Sn and Zr are more preferred. Al, Si, Ti and Zr are further preferred, and Si is especially preferred.

The hydrolyzable group in the metal compound (b) may be a group same as the hydrolyzable group in the organosilicon compound (a), and is preferably an alkoxy group with a carbon number of 1 to 4, more preferably an alkoxy group with a carbon number of 1 or 2. The hydrolyzable groups in the organosilicon compound (a) and the metal compound (b) may be the same or different, but are preferably the same. Each of the hydrolyzable groups in the organosilicon compound (a) and the metal compound (b) is preferably an alkoxy group with a carbon number of 1 to 4.

In the metal compound (b), the number of hydrolyzable groups is preferably not less than 1, more preferably not less than 2, further preferably not less than 3, and is preferably not more than 4.

The siloxane containing group and the hydrocarbon chain-containing group in the metal compound (b) can be appropriately selected from the groups described above, and the number of the groups is preferably not more than 1, especially preferably 0.

Specifically, the metal compound (b) is preferably a compound represented by any one of the following formulae (II-1) to (II-3), more preferably a compound represented by the formula (II-1). The compound represented by any one of the formulae (II-1) to (II-3) may be a hydrolysis condensation product thereof. Here, the hydrolysis condensation product means a compound formed by condensing all or a part of hydrolyzable groups in each of compounds (II-1) to (II-3) by hydrolysis.

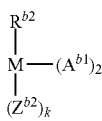
(II-1)

wherein M represents a trivalent or tetravalent metal atom capable of foiling a metal alkoxide;

each of $A^{b1}$ independently represents a hydrolyzable group;

$Z^{b2}$ represents a siloxane containing group, a hydrocarbon chain-containing group or a hydrolyzable group;

$R^{b2}$ represents a siloxane containing group, a hydrocarbon chain-containing group or a hydrolyzable group, $R^{b2}$ and $Z^{b2}$ may be the same or different when $R^{b2}$ and $Z^{b2}$ represent a siloxane containing group or a hydrocarbon chain-containing group, and $R^{b2}$ and $A^{b1}$ may be the same or different when $Z^{b2}$ represents a hydrolyzable group, and $R^{b2}$ and $Z^{b2}$ may be the same or different among a plurality of formulae (II-1); and k represents an integer of 0 or 1 depending on M.

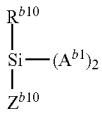
(II-2)

wherein $R^{b10}$ represents a fluorine-containing alkyl group with a carbon number of 1 to 8;

each of $A^{b1}$ independently represents a hydrolyzable group;

$Z^{b10}$ represents a siloxane containing group, hydrocarbon chain-containing group or a hydrolyzable group, and $R^{b10}$ and $Z^{b10}$ may be the same or different among plurality of formulae (II-2).

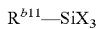
$R^{b11}$—$SiX_3$ (II-3)

wherein $R^{b11}$ represents a hydrolizable silane oligomer residue; and each of X independently represents a hydrolizable group, a fluorine-containing alkyl group with a carbon number of 1 to 12 or an alkyl group with a carbon number of 1 to 4.

In the formula (II-1), the siloxane containing group of $R^{b2}$ or $Z^{b2}$, the hydrocarbon chain-containing group and the hydrolyzable group of $R^{b2}$, $A^{b1}$ or $Z^{b2}$ can be appropriately selected from the groups described above as the siloxane containing group, the hydrocarbon chain-containing group and the hydrolyzable group, respectively. The fluorine-containing alkyl group of $R^{b2}$ can be appropriately selected from the groups described above as the fluorine-containing alkyl group of $R^{b1}$ and the hydrolyzable silane oligomer residue.

In particular, $R^{b2}$ is preferably a siloxane containing group or a hydrolyzable group, more preferably a hydrolyzable group. $Z^{b2}$ is preferably a siloxane containing group or a hydrolyzable group, more preferably a hydrolyzable group.

Each of $R^{b2}$ and $Z^{b2}$ is preferably a hydrolyzable group. Here, it is preferred that $R^{b2}$ and $A^{b1}$ are the same hydrolyzable group, and it is more preferred that $R^{b2}$, $A^{b1}$ and $Z^{b2}$ are the same hydrolyzable group.

The hydrolyzable groups in the organosilicon compound (a) and the metal compound (b) may be the same group, and are each more preferably an alkoxy group with a carbon number of 1 to 4.

In the formula (II-1), the metal M is preferably a trivalent metal such as Al or a tetravalent metal such as Si, Ti, Zr or Sn, more preferably Si, Al, Ti or Zr, especially preferably Si. The alkoxide of such a metal is easily liquefied, so that the uniformity of the distribution of the structure (B) in the transparent film is easily improved. k represents 0 when M is a trivalent metal, and k represents 1 when M is a tetravalent metal.

The ratio of metal compounds other than the compound represented by any one of the formulae (II-1) to (II-3) and a hydrolysis condensation product thereof is preferably not more than 10% by mass, more preferably not more than 5% by mass, further preferably not more than 2% by mass, especially preferably not more than 1% by mass based on 100% by mass of the metal compound (b).

Examples of the metal compound (b) may include compounds having only one hydrolyzable group; compounds having one siloxane containing group and one hydrolyzable group; compounds having two siloxane containing groups and one hydrolyzable group; compounds having one hydrocarbon chain-containing group and a hydrolyzable group; compounds having two hydrocarbon chain-containing groups and one hydrolyzable group; compounds in which one fluorine-containing alkyl group and one hydrolyzable group are bonded to a silicon atom; and hydrolyzable silane oligomers.

Examples of the compound having only the hydrolyzable group include tetraalkoxysilanes such as tetramethoxysilane, tetraethoxysilane, tetrapropoxysilane and tetrabutoxysilane; trialkoxyaluminums such as triethoxyaluminum, tripropoxyaluminum and tributoxyaluminum; trialkoxyirons such as triethoxyiron; trialkoxyindiums such as trimethoxyindium, triethoxyindium, tripropoxyindium and tributoxyindium; tetraalkoxyhafniums such as tetramethoxyhafnium, tetraethoxyhafnium, tetrapropoxyhafnium and tetrabutoxyhafnium; tetraalkoxytitaniums such as tetramethoxytitanium, tetraethoxytitanium, tetrapropoxytitanium and tetrabutoxytitanium; tetraalkoxytins such as tetramethoxytin, tetraethoxytin, tetrapropoxytin and tetrabutoxytin; tetraalkoxyzirconiums such as tetramethoxyzirconium, tetraethoxyzirconium, tetrapropoxyzirconium and tetrabutoxyzirconium; and pentaalkoxytantalums such as pentamethoxytantalum, pentaethoxytantalum, pentapropoxytantalum and pentabutoxytantalum.

Examples of the compound having a siloxane containing group and a hydrolyzable group include trimethylsilyloxy trialkoxysilanes such as trimethylsilyloxy trimethoxysilane, trimethylsilyloxy triethoxysilane and trimethylsilyloxy tripropoxysilane.

Examples of the compound having two siloxane containing groups and a hydrolyzable group include di(trimethylsilyloxy)dialkoxysilanes such as di(trimethylsilyloxy)dimethoxysilane, di(trimethylsilyloxy)diethoxysilane and di(trimethylsilyloxy)ditripropoxysilane.

Examples of the compound having a hydrocarbon chain-containing group and a hydrolyzable group include alkyltrialkoxysilanes such as methyltrimethoxysilane, ethyltrimethoxysilane, methyltriethoxysilane, ethyltriethoxysilane and methyltripropoxysilane; and alkenyltrialkoxysilanes such as vinyltrimethoxysilane and vinyltriethoxysilane.

Examples of the compound having two hydrocarbon chain-containing groups and a hydrolyzable group include dialkyldialkoxysilanes such as dimethyldimethoxysilane, diethyldimethoxysilane, dimethyldiethoxysilane and diethyldiethoxysilane.

Examples of the compound in which a fluorine-containing alkyl group and a hydrolyzable group are bonded to a silicon atom include $CF_3—Si—(OCH_3)_3$ and $C_{r1}F_{2r1+1}—Si—(OC_2H_5)_3$ (r1 is preferably an integer of 1 to 15, more preferably an integer of 1 to 12, further preferably an integer of 1 to 6), and among them, particularly $C_4F_9—Si—(OC_2H_5)_3$, $C_6F_{13}—Si—(OC_2H_5)_3$, $C_7F_{15}—Si—(OC_2H_5)_3$ and $C_8F_{17}—Si—(OC_2H_5)_3$ are preferred. Examples of the above compound further include $CF_3CH_2O(CH_2)_{r2}SiCl_3$, $CF_3CH_2O(CH_2)_{r2}Si(OCH_3)_3$, $CF_3CH_2O(CH_2)_{r2}Si(OC_2H_5)_3$, $CF_3(CH_2)_{r3}Si(CH_3)_2(CH_2)_{r2}SiCl_3$, $CF_3(CH_2)_{r3}Si(CH_3)_2(CH_2)_{r2}Si(OCH_3)_3$, $CF_3(CH_2)_{r3}Si(CH_3)_2(CH_2)_{r2}Si(OC_2H_5)_3$, $CF_3COO(CH_2)_{r2}SiCl_3$, $CF_3COO(CH_2)_{r2}Si(OCH_3)_3$ and $CF_3COO(CH_2)_{r2}Si(OC_2H_5)_3$ (each of r2 is 5 to 20, preferably 8 to 15, and r3 is 1 to 7, preferably 2 to 6). Examples of the above compound may also include $CF_3(CF_2)_{r4}—(CH_2)_{r5}SiCl_3$, $CF_3(CF_2)_{r4}—(CH_2)_{r5}Si(OCH_3)_3$ and $CF_3(CF_2)_{r4}—(CF_{12})_{r5}Si(OC_2H_5)$ (r4 is 1 to 10, preferably 2 to 8, more preferably 2 to 5, and r5 is 1 to 5, preferably 2 to 4). Examples of the above compound may also include $CF_3(CF_2)_{r6}—(CH_2)_{r7}—Si—(CH_2CH=CH_2)_3$ (each of r6 is 2 to 10, preferably 2 to 8, and each of r7 is 1 to 5, preferably 2 to 4).

Examples of the above compound also include $CF_3(CF_2)_{r8}—(CH_2)_{r9}SiCH_3Cl_2$, $CF_3(CF_2)_{r8}—(CH_2)_{r9}SiCH_3(OCH_3)_2$ and $CF_3(CF_2)_{r8}—(CH_2)_{r9}SiCH_3(OC_2H_5)_2$ (each of r8 is 2 to 10, preferably 3 to 7, and each of r9 is 1 to 5, preferably 2 to 4).

Examples of the hydrolyzable silane oligomer include $(H_5C_2O)_3—Si—(OSi(OC_2H_5)_2)_4OC_2H_5$ and $(H_3CO)_2—Si(CH_2CH_2CF_3)—(OSiOCH_3(CH_2CH_2CF_3))_4—OCH_3$.

Among them, compounds having only one hydrolyzable group; compounds having one siloxane containing group and one hydrolyzable group; compounds having two siloxane containing groups and one hydrolyzable group; compounds having one hydrocarbon chain-containing group and one hydrolyzable group; and compounds having two hydrocarbon chain-containing groups and one hydrolyzable group are preferred, and compounds having only one hydrolyzable group are more preferred.

The molar ratio of the metal compound (b) to the organosilicon compound (a) as metal compound (b)/organosilicon compound (a) is preferably not less than 0.1, more preferably not less than 1, still more preferably not less than 5, further preferably not less than 8, and preferably not more than 100, more preferably not more than 80, still more preferably not more than 70, further preferably not more than 60, especially preferably not more than 50.

Examples of the preferred aspect of the coating composition include the following aspects.

In a first preferred aspect, the metal compound (b) is at least one selected from the group consisting of a compound in which the carbon number of the fluorine-containing alkyl group represented by $R^{b10}$ is 1 to 8 (preferably 1 to 6) among compounds represented by the following formula (II-2), and a hydrolysis condensation product thereof.

wherein $A^{b1}$, $R^{b10}$ and $Z^{b10}$ represent the same meaning as above, respectively.

Here, the organosilicon compound (a) is preferably a compound represented by the following formula (I-II).

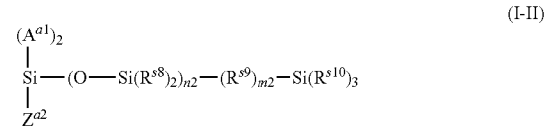

wherein $A^{a1}$, $Z^{a2}$, $R^{s8}$, $R^{s9}$, $R^{s10}$, m2 and n2 represent the same meaning as above, respectively.

In this aspect, the molar ratio of the organosilicon compound (a) to the metal compound (b) as metal compound (b)/organosilicon compound (a) is preferably not less than 0.1, more preferably not less than 5, further preferably not less than 8, and preferably not more than 80, more preferably not more than 60, further preferably not more than 50.

In a second preferred aspect, the metal compound (b) is at least one selected from a compound represented by the following formula (II-1) and a hydrolysis condensation product thereof, and the molar ratio of the metal compound (b) to the organosilicon compound (a) as metal compound (b)/organosilicon compound (a) is not less than 10.

$R^{b2}$, $A^{b1}$, $Z^{b2}$ and k represent the same meaning as above, respectively.

Here, the organosilicon compound (a) is preferably a compound represented by the following formula (I-II).

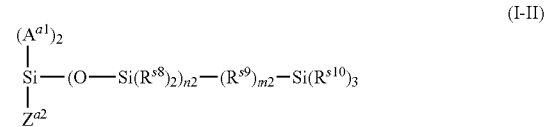

$A^{a1}$, $Z^{a2}$, $R^{s8}$, $R^{s9}$, $R^{s10}$, m2 and n2 represent the same meaning as above, respectively.

In this aspect, the molar ratio of the metal compound (b) to the organosilicon compound (a) as metal compound (b)/organosilicon compound (a) is not less than 10, preferably not less than 15, more preferably not less than 18. The molar ratio as metal compound (b)/organosilicon compound (a) is preferably not more than 80, more preferably not more than 60, further preferably not more than 50.

In a third preferred aspect, the organosilicon compound is a compound represented by the following formula (I-I).

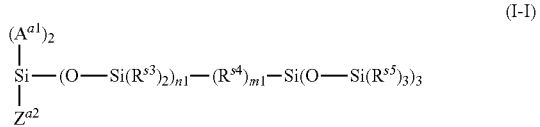

$$\text{(I-I)}$$

$A^{a1}$, $Z^{a2}$, $R^{s3}$, $R^{s4}$, $R^{s5}$, m1 and n1 represent the same meaning as above, respectively.

In this aspect, the molar ratio of the organosilicon compound (a) to the metal compound (b) as metal compound (b)/organosilicon compound (a) is preferably not less than 0.1, more preferably not less than 5, further preferably not less than 8, and preferably not more than 80, more preferably not more than 60, further preferably not more than 50.

Examples of the solvent (c) for diluting the organosilicon compound (a) and the metal compound (b) include hydrophilic organic solvents such as alcohol-based solvents, ether-based solvents, ketone-based solvents, ester-based solvents, amide-based solvents and water. These solvents may be used singly, or used in combination of two or more thereof.

Examples of the alcohol-based solvent include methanol, ethanol, propanol, isopropyl alcohol, butanol, ethylene glycol, propylene glycol and diethylene glycol; examples of the ether-based solvent include dimethoxy ethane, tetrahydrofuran and dioxane; examples of the ketone-based solvent include acetone and methyl ethyl ketone; examples of the ester-based solvent include ethyl acetate and butyl acetate; and examples of the amide-based solvent include dimethylformamide.

In particular, alcohol-based solvents and ketone-based solvents are preferred, and these solvents may contain water.

The amount of the solvent (c) is preferably not less than 0.01 parts by mass, more preferably not less than 0.05 parts by mass, further preferably not less than 0.1 parts by mass, and preferably not more than 20 parts by mass, more preferably not more than 10 parts by mass, further preferably not more than 5 parts by mass based on 1 part by mass of the total of the organosilicon compound (a) and the metal compound (b). When the amount of the solvent (c) is in a range as described above, the thickness of the transparent film is easily controlled.

A catalyst (d) may coexist at the time of contacting the organosilicon compound (a) and the metal compound (b) with a substrate. The catalyst (d) should act as a hydrolysis catalyst for hydrolyzable groups that are bonded to a silicon atom, and examples of the catalyst (d) include acidic compounds; basic compounds; and organometallic compounds. Examples of the acidic compound include inorganic acids such as hydrochloric acid and nitric acid; and organic acids such as acetic acid. Examples of the basic compound include ammonia and amine. The organometallic compound comprises a metal element such as Al, Fe, Zn or Sn as a center metal, and examples thereof include organoaluminum compounds such as aluminum-acetylacetone complexes and aluminum-ethyl acetoacetate complexes; organoiron compounds such as iron octylate; organozinc compounds such as zinc acetylacetonate monohydrate, zinc naphthenate and zinc octylate; and organotin compounds such as dibutyl tin diacetate complexes.

In particular, the catalyst (d) is preferably an organometallic compound or an acidic compound, more preferably an organoaluminum compound or hydrochloric acid.

The amount of the catalyst (d) is preferably not less than 0.0001 parts by mass, more preferably not less than 0.0002 parts by mass, further preferably not less than 0.001 parts by mass, and preferably not more than 20 parts by mass, more preferably not more than 10 parts by mass, further preferably not more than 5 parts by mass based on 100 parts by mass of the total of the organosilicon compound (a) and the metal compound (b).

When an acidic compound is used as a catalyst, the amount of the catalyst (d) is preferably not less than 0.001 parts by mass, more preferably not less than 0.005 parts by mass, further preferably not less than 0.01 parts by mass, and preferably not more than 1 part by mass, more preferably not more than 0.5 parts by mass based on 100 parts by mass of the total of the organosilicon compound (a) and the metal compound (b).

When an organometallic compound is used as a catalyst, the amount of the catalyst (d) is preferably not less than 0.0001 parts by mass, more preferably not less than 0.0002 parts by mass, further preferably not less than 0.001 parts by mass, and preferably not more than 0.1 parts by mass, more preferably not more than 0.05 parts by mass based on 100 parts by mass of the total of the organosilicon compound (a) and the metal compound (b).

Further, at the time of contact of the organosilicon compound (A) and the metal compound (B) to a substrate, various kinds of additives such as an antioxidant, a rust inhibitor, an ultraviolet absorber, a light stabilizer, an antifungal agent, an antibacterial agent, an organism deposition preventing agent, a deodorizer, a pigment, a flame retardant and an antistatic agent may coexist.

Examples of the antioxidant include phenol-based antioxidants, sulfur-based antioxidants, phosphorus-based antioxidants and hindered amine-based antioxidants.

Examples of the phenol-based antioxidant include n-octadecyl-3-(4-hydroxy-3,5-di-t-butylphenyl)propionate, 2,6-di-t-butyl-4-methylphenol, 2,2-thio-diethylene-bis-[3-(3,5-di-t-butyl-4-hydroxyphenyl)propionate], tri-ethyleneglycol-bis-[3-(3-t-butyl-5-methyl-4-hydroxyphenyl)propionate], 3,9-bis[2-{3-(3-t-butyl-4-hydroxy-5-methylphenyl)propionyloxy}-1,1-dimethylethyl]-2,4,8,10-tetraoxaspiro[5.5]undecane, tetrakis{3-(3,5-di-t-butyl-4-hydroxyphenyl)-propionic acid}pentaerythrityl esters, 2-t-butyl-6-(3-t-butyl-2-hydroxy-5-methylbenzyl)-4-methylphenyl acrylate, 2-[1-(2-hydroxy-3,5-di-t-pentylphenyl)ethyl]-4,6-di-t-pentylphenyl acrylate, 1,3,5-trimethyl-2,4,6-tris(3,5-di-t-butyl-4-hydroxybenzyl)benzene, tris(3,5-di-t-butyl-4-hydroxybenzyl) isocyanurate, 1,3,5-tris(4-t-butyl-3-hydroxy-2,6-dimethylbenzyl)-1,3,5-triazine-2,4,6-(1H,3H,5H)-trione, 2,2'-methylenebis(6-t-butyl-4-methylphenol), 4,4'-butylidenebis (6-t-butyl-3-methylphenol) and 4,4'-thiobis(6-t-butyl-3-methylphenol).

Examples of the sulfur-based antioxidant include 3,3'-thiodipropionic acid di-n-dodecyl esters, 3,3'-thiodipropionic acid di-n-tetradecyl esters, 3,3'-thiodipropionic acid di-n-octadecyl esters and tetrakis(3-dodecylthiopropionic acid) pentaerythritol esters.

Examples of the phosphorus-based antioxidant include tris(2,4-di-t-butylphenyl)phosphite, bis(2,4-di-t-butylphenyl)pentaerythritol diphosphite, bis(2,6-di-t-butyl-4-methylphenyl)pentaerythritol diphosphite, bis(2,4-di-cumylphenyl)pentaerythritol diphosphite, tetrakis(2,4-di-t-butylphenyl)-4,4'-biphenylene diphosphonite and bis-[2,4-di-t-butyl-(6-methyl)phenyl]ethyl phosphite.

Examples of the hindered amine-based antioxidant include sebacic acid bis(2,2,6,6-tetramethyl-4-piperidyl)esters (melting point: 81 to 86° C.), 2,2,6,6-tetramethyl-4-piperidyl methacrylate (melting point: 58° C.), and poly[{6-(1,1,3,3-tetramethylbutyl)amino-1,3,5-triazine-2,4-diyl}{

(2,2,6,6-tetramethyl-4-piperidyl)imino}-1,6-hexamethylene{(2,2,6,6-tetramethyl-4-piperidyl)imino}].

Examples of the rust inhibitor include alkanol amines such as triethanol amine; quaternary ammonium salts; alkanethiols; azoles such as imidazoline, imidazole, alkylimidazoline derivatives, benzimidazole, 2-mercaptobenzimidazole and benzotriazole; sodium metavanadate; bismuth citrate; phenol derivatives; amine compounds such as aliphatic amines including alkylamines and polyalkenylamines, aromatic amines, ethoxylated amines, cyanoalkylamines, cyclohexylamine benzoate, aliphatic diamines such as alkylenediamines, and aromatic diamines; amides of the amine compounds and carboxylic acid; alkyl esters; pyrimidine; naphthenic acid; sulfonic acid composites; nitrous acid salts such as calcium nitrite, sodium nitrite and dicyclohexylamine nitrite; polyol compounds such as polyalcohols and polyphenols; heteropolyacid salts such as sodium molybdate, sodium tungstate, sodium phosphonate, sodium chromate and sodium silicate; gelatin; polymers of carboxylic acid; nitro compounds; formaldehyde; acetylene alcohol; thiol compounds such as aliphatic thiols, aromatic thiols and acetylene thiols; sulfide compounds such as aliphatic sulfide, aromatic sulfide and acetylene sulfide; sulfoxide compounds such as sulfoxide and dibenzylsulfoxide; thio urea; combinations of an amine or quaternary ammonium salt and halogen ions; combinations of an alkylamine and potassium iodide; combinations of tannin and sodium phosphate; combinations of triethanolamine and laurylsarcosine; combinations of triethanolamine, laurylsarcosine and benzotriazole; and combinations of an alkylamine, benzotriazole, sodium nitrite and sodium phosphate.

Examples of the ultraviolet absorber/light stabilizer include for example 2-(5-methyl-2-hydroxyphenyl)benzotriazole, 2-[2-hydroxy-3,5-bis(α,α-dimethylbenzyl)phenyl]-2H-benzotriazole, 2-(3-t-butyl-5-methyl-2-hydroxyphenyl)-5-chlorobenzotriazole, 2-(2'-hydroxy-5'-t-octylphenyl) benzotriazole, condensation products of methyl-3-[3-t-butyl-5-(2H-benzotriazol-2-yl)-4-hydroxyphenyl] propionate-polyethylene glycol (molecular weight: about 300), hydroxyphenyl benzotriazole derivatives, 2-(4,6-diphenyl-1,3,5-triazin-2-yl)-5[(hexyl)oxy]-phenol and 2-ethoxy-2'-ethyl-oxalic acid bisanilide.

Examples of the antifungal agent/antibacterial agent include 2-(4-thiazolyl)benzimidazole, sorbic acid, 1,2-benzisothiazolin-3-one, (2-pyridylthio-1-oxide)sodium, dehydroacetic acid, 2-methyl-5-chloro-4-isothiazolone complexes, 2,4,5,6-tetrachlorophthalonitrile, methyl 2-benzimidazolecarbamate, methyl 1-(butylcarbamoyl)-2-benzimidazolecarbamate, mono- or dibromocyanoacetamides, 1,2-dibromo-2,4-dicyanobutane, 1,1-dibromo-1-nitropropanol and 1,1-dibromo-1-nitro-2-acetoxypropane.

Examples of the organism deposition preventing agent include tetramethylthiuram disulfide, zinc bis(N,N-dimethyldithiocarbamate), 3-(3,4-dichlorophenyl)-1,1-dimethylurea, dichloro-N-((dimethylamino)sulfonyl)fluoro-N—(P-tryl)methanesulpheneamide, pyridine-triphenylborane, N,N-dimethyl-N'-phenyl-N'-(fluorodichloromethylthio)sulfamide, cuprous thiocyanate (1), cuprous oxide, tetrabutylthiuram disulfide, 2,4,5,6-tetrachloroisophthalonitrile, zinc ethylenebisdithiocarbamate, 2,3,5,6-tetrachloro-4-(methylsulfonyl)pyridine, N-(2,4,6-trichlorophenyl)maleimide, bis(2-pyridinethiol-1-oxide)zinc salts, bis(2-pyridinethiol-1-oxide)copper salts, 2-methylthio-4-t-butylamino-6-cyclopropylamino-s-triazine, 4,5-dichloro-2-n-octyl-4-isothiazolin-3-one, furanones, alkylpyridine compounds, gramine-based compounds and isotonyl compounds.

Examples of the deodorizer include organic acids such as lactic acid, succinic acid, malic acid, citric acid, maleic acid, malonic acid, ethylenediamine polyacetic acid, alkane-1,2-dicarboxylic acids, alkene-1,2-dicarboxylic acids, cycloalkane-1,2-dicarboxylic acids, cycloalkene-1,2-dicarboxylic acids and naphthalene sulfonic acid; fatty acid metals such as zinc undecylenate, zinc 2-ethyl hexanoate and zinc ricinoleate; metal compounds such as iron oxide, iron sulfate, zinc oxide, zinc sulfate, zinc chloride, silver oxide, copper oxide, metal (iron, copper or the like) chlorophyllin sodium, metal (iron, copper, cobalt or the like) phthalocyanine, metal (iron, copper, cobalt or the like) tetrasulfonic acid phthalocyanine, titanium dioxide and visible light-responsive titanium dioxide (nitrogen-doped-type or the like); cyclodextrins such as α-, β- or γ-cyclodextrin, methyl derivatives thereof, hydroxypropyl derivatives, glucosyl derivatives and maltosyl derivatives; and porous materials such as acrylic acid-based polymers including porous methacrylic acid polymers and porous acrylic acid polymers, aromatic-based polymers including porous divinylbenzene polymers, porous styrene-divinylbenzene-vinylpyridine polymers and porous divinylbenzene-vinylpyridine polymers, copolymers thereof, chitin, chitosan, activated carbon, silica gel, activated alumina, zeolite and ceramics.

Examples of the pigment include carbon black, titanium oxide, phthalocyanine-based pigments, quinacridone-based pigments, isoindolinone-based pigments, perylene or perynine-based pigments, quinophthalone-based pigments, diketopyrrolo-pyrrole-based pigments, dioxazine-based pigments, disazo-condensed-based pigments and benzimidazolone-based pigments.

Examples of the flame retardant include decabromobiphenyl, antimony trioxide, phosphorus-based flame retardants and aluminum hydroxide.

Examples of the antistatic agent include cationic surfactants of quaternary ammonium salt type; amphoteric surfactants of betaine type; anionic surfactants of alkyl phosphate type; cationic surfactants such as primary amine salts, secondary amine salts, tertiary amine salts, quaternary amine salts and pyridine derivatives; anionic surfactants such as sulfated oil, soap, sulfated ester oil, sulfated amide oil, sulfated ester salts of olefins, fatty alcohol sulfuric acid ester salts, alkylsulfuric acid ester salts, fatty acid ethyl sulfonic acid salts, alkylnaphthalene sulfonic acid salts, alkylbenzene sulfonic acid salts, succinic acid ester sulfonic acid salts and phosphoric acid ester salts; nonionic surfactants such as partial fatty acid esters of polyhydric alcohols, ethylene oxide adducts of fatty alcohols, ethylene oxide adducts of fatty acids, ethylene oxide adducts of fatty amino or fatty acid amides, ethylene oxide adducts of alkylphenols, ethylene oxide adducts of partial fatty acid esters of polyhydric alcohols and polyethylene glycol; and amphoteric surfactants such as carboxylic acid derivatives and imidazoline derivatives.

As additives, a lubricant, a filler, a plasticizer, a nucleating agent, an antiblocking agent, a foaming agent, an emulsifier, a brightening agent, a binder and the like may further coexist.

When these additives are contained, the content of the additives is normally 0.1 to 70% by mass, preferably 0.1 to 50% by mass, more preferably 0.5 to 30% by mass, further preferably 2 to 15% by mass in the coating composition containing the organosilicon compound (A) and the metal compound (B).

The content of the total of the organosilicon compound (a) and the metal compound (b) (the total of the organosilicon compound (a), the metal compound (b) and the solvent (c)

when the solvent (c) is contained) is normally not less than 60% by mass, preferably not less than 75% by mass, more preferably not less than 85% by mass, further preferably not less than 95% by mass in the coating composition.

Examples of the method for contacting the organosilicon compound (a) and the metal compound (b) with a substrate include a spin coating method, a dip coating method, a spray coating method, a roll coating method, a bar coating method and a die coating method, and a spin coating method or spray coating method is preferred. According to the spin coating method or spray coating method, a transparent film having a predetermined thickness is easily formed.

Here, the coating composition may be further diluted as necessary. The dilution ratio is, for example, 2 to 100, preferably 5 to 50 with respect to the composition before dilution. As the dilution solvent, a solvent as shown as an example of the solvent (c) can be appropriately used.

When the organosilicon compound (a) and the metal compound (b) are placed in air while being in contact with a substrate, moisture in the air is captured, so that the hydrolyzable group is hydrolyzed to form a siloxane backbone. The placement may be performed at 40 to 250° C.

The transparent film of the present invention thus obtained is superior in weather resistance to a conventional film those obtained from a fluorine coating agent.

The transparent film of the present invention comprises a trialkylsilyl containing molecular chain or a molecular chain in which alkyl groups in a trialkylsilyl containing molecular chain are replaced by fluoroalkyl groups and also the change in contact angle thereof is controlled to a specific range before and after thermal history or before and after photoirradiation. Thus, the transparent film of the present invention has high chemical/physical durability and excellent abrasion resistance. The abrasion resistance can be evaluated by, for example, an abrasion test using an eraser.

The transparent film of the present invention is also excellent in liquid droplet slide behavior. The slide behavior of liquid droplet can be determined by, for example, placing a liquid droplet on the transparent film of the present invention, and measuring the slide-falling speed of the liquid droplet at inclination of the transparent film from horizontal angle to an angle of 90°.

Since the transparent film of the present invention has high chemical/physical durability and is excellent in liquid droplet slide behavior, the transparent film also exhibits excellent slide behavior when rubbed with a finger.

The transparent film of the present invention is normally formed on a substrate, and a substrate comprising the transparent film of the present invention on the surface is also encompassed in the scope of the present invention. The substrate may be in the form of a flat surface or a curved surface, or may have a three-dimensional structure in which a large number of surfaces are combined. The substrate may be formed of an organic material or an inorganic material. Examples of the organic material include thermoplastic resins such as acrylic resin, polycarbonate resin, polyester resin, styrene resin, acryl-styrene copolymer resin, cellulose resin, polyolefin resin and polyvinyl alcohol resin; and thermosetting resins such as phenol resin, urea resin, melamine resin, epoxy resin, unsaturated polyester, silicone resin and urethane resin. Examples of the inorganic material include ceramics; glass; metals such as iron, silicon, copper, zinc and aluminum; and alloys including the above metals.

The substrate may be subjected to an easy adhesion treatment beforehand. Examples of the easy adhesion treatment include hydrophilization treatments such as a corona treatment, a plasma treatment and an ultraviolet-ray treatment. A primer treatment with a resin, a silane coupling agent, a tetraalkoxysilane or the like may also be employed. By providing a primer layer between a water-repellent film and a substrate by the primer treatment, durability such as moisture resistance and alkali resistance can be further improved.

The primer layer is preferably a layer formed using an under-layer forming composition containing a component (P) capable of forming a siloxane backbone.

The primer layer is preferably a layer formed using an under-layer forming composition containing a component (P1) composed of a compound represented by the following formula (III), and/or a partial hydrolysis condensation product thereof.

$$Si(X^{P2})_4 \qquad (III)$$

wherein each of $X^{P2}$ independently represents a halogen atom, an alkoxy group or an isocyanate group.

In the formula (III), $X^{P2}$ is preferably a chlorine atom, an alkoxy group with a carbon atom number of 1 to 4, or isocyanate group, and four $X^{P2}$s are preferably the same.

Specifically, $Si(NCO)_4$, $Si(OCH_3)_4$, $Si(OC_2H_5)_4$ or the like is preferably used as the compound represented by the general formula (III) (hereinafter, sometimes referred to as a compound (III)). In the present invention, the compounds (III) may be used singly, or used in combination of two or more thereof.

The component (P1) contained in the primer layer forming composition may be a partial hydrolysis condensation product of the compound (III). The partial hydrolysis condensation product of the compound (III) can be obtained by applying a general hydrolysis condensation method using an acid or base catalyst. The degree of condensation (degree of polymerization) of the partial hydrolysis condensation product is required to be a degree which allows a product to be dissolved in a solvent. The component (P1) may be the compound (III), or a partial hydrolysis condensation product of the compound (III), or may be a mixture of the compound (III) and a partial hydrolysis condensation thereof, for example, a partial hydrolysis condensation product of the compound (III) containing an unreacted part of the compound (III). As the compound represented by the general formula (III) or the partial hydrolysis condensation product, a commercial product is available, and such a commercial product can be used in the present invention.

The under-layer forming composition may be a composition containing the component (P1), and a component (P2) composed of a compound represented by the following formula (IV) (hereinafter, referred to as a compound (IV)) and/or a partial hydrolysis condensation product thereof, or a composition containing a partial hydrolysis co-condensation product of the component (P1) and component (P2) (which may contain the component (P1) and/or the compound (IV)).

$$X^{P3}_3Si-(CH_2)_p-SiX^{P3}_3 \qquad (IV)$$

wherein each of $X^{P3}$ independently represents a hydrolyzable group or a hydroxyl group, and p is an integer of 1 to 8.

The compound (IV) is a compound having a hydrolyzable silyl group or silanol group at both ends of a divalent organic group.

Examples of the hydrolyzable group represented by $X^{P3}$ in the formula (IV) include the same group or atom as $X^{P2}$. $X^{P3}$ is preferably an alkoxy group or isocyanate group, especially preferably an alkoxy group from the viewpoint of stability of the compound (IV) and ease of hydrolysis. The alkoxy group is preferably an alkoxy group with a carbon atom number of 1 to 4, more preferably methoxy group or ethoxy group. These groups are appropriately selected according to the purpose, use and the like in production. A plurality of $X^{P3}$ existing in the compound (IV) may be the same or different, and is preferably the same from the viewpoint of easy availability.

Specific examples of the compound (IV) include $(CH_3O)_3SiCH_2CH_2Si(OCH_3)_3$, $(OCN)_3SiCH_2CH_2Si(NCO)_3$, $Cl_3SiCH_2CH_2SiCl_3$, $(C_2H_5O)_3SiCH_2CH_2S(OC_2H_5)_3$, $(CH_3O)_3SiCH_2CH_2CH_2CH_2CH_2CH_2Si(OCH_3)_3$, or the like. In the present invention, the compounds (IV) may be used singly, or used in combination of two or more thereof.

The component contained in the primer layer forming composition may be a partial hydrolysis condensation product of the compound (IV). The partial hydrolysis condensation product of the compound (IV) can be obtained by the same method as described in the production of the partial hydrolysis condensation product of the compound (III). The degree of condensation (degree of polymerization) of the partial hydrolysis condensation product is required to be a degree which allows a product to be dissolved in a solvent. The component (P) may be the compound (IV), or the partial hydrolysis condensation product of the compound (III), or may be a mixture of the compound (IV) and a partial hydrolysis condensation thereof, for example a partial hydrolysis condensation product of the compound (IV) containing an unreacted part of the compound (IV).

As the compound represented by the general formula (IV) or the partial hydrolysis condensation product, a commercial product is available, and such a commercial product can be used in the present invention.

For the under-layer, various kinds of polysilazanes capable of forming an oxide film mainly composed of silicon, which is similar to the compound (III), may be used.

The primer layer forming composition normally contains an organic solvent in addition to a solid as a layer forming component in consideration of economic efficiency, workability and ease of controlling the thickness of the obtained primer layer. The organic solvent is not particularly limited as long as it is capable of dissolving a solid contained in the primer layer forming composition. Examples of the organic solvent include the same compounds as in the water-repellent film forming composition. The organic solvent is not limited to one kind of solvent, and two or more solvents different in polarity, vaporization rate and so on may be mixed and used.

When the primer layer forming composition contains a partial hydrolysis condensation product and a partial hydrolysis co-condensation product, the primer layer forming composition may contain a solvent used for producing these condensation products.

Further, it is preferable that for accelerating a hydrolysis co-condensation reaction, a catalyst such as an acid catalyst which is similar to one that is generally used in a partial hydrolysis condensation reaction is blended even in a primer layer forming composition which does not contain a partial hydrolysis condensation product and a partial hydrolysis co-condensation product. In the case where the primer layer forming composition contains a partial hydrolysis condensation product and a partial hydrolysis co-condensation product, a catalyst is preferably blended when a catalyst used in these condensation products does not remain in the composition.

The under-layer forming composition may contain water for carrying out a hydrolysis condensation reaction and hydrolysis co-condensation reaction of the contained component.

As a method for forming an under-layer using the primer layer forming composition, a known method with an organosilane compound-based surface treatment agent can be used. For example, the under-layer forming composition can be applied to a surface of a base by a method such as brush coating, flow coating, rotation coating, immersion coating, squeeze coating, spray coating or hand coating, dried as necessary in the air or a nitrogen atmosphere, and then cured to form the under-layer. Conditions for curing are appropriately controlled according to the kind, concentration and the like of a composition to be used.

Curing of the primer layer forming composition may be performed concurrently with curing of a water-repellent film forming composition.

The thickness of the primer layer is not particularly limited as long as it ensures that moisture resistance, adhesion and barrier property to an alkali etc. from the substrate can be imparted to a water-repellent film formed on the primer layer.

The transparent film of the present invention attains both water/oil repellency and hardness, and is useful as a base material in display devices such as touch panel displays, optical elements, semiconductor elements, building materials, automobile components, nanoimprint techniques, solar cell members and so on. The transparent film of the present invention is suitably used for articles such as bodies, window glass (windshield, side glass and rear glass), mirrors and bumpers in transportation equipment such as trains, automobiles, watercrafts and aircrafts. The transparent film can also be used in outdoor applications such as building outer walls, tents, solar cell power generation modules, sound insulating boards and concrete. The transparent film can also be used in fishing nets, bug catching nets and water tanks. Further, the transparent film can also be used in various kinds of indoor equipment such as articles of members around kitchens, bathrooms, washbasins, mirrors and toilets, chandeliers, potteries such as tiles, artificial marbles, and air conditioners. Further, the transparent film can also be used for antifouling treatment of tools, inner walls, pipes and so on in factories. The transparent film is also suitable for goggles, glasses, helmets, pinball games, fibers, umbrellas, play equipment, soccer balls and so on. Further, the transparent film can also be used as a deposition preventing agent for various kinds of packaging materials such as food packaging materials, cosmetic packaging materials and interiors of pots.

The present application claims the benefit of priority to Japanese patent application No. 2014-223651 filed on Oct. 31, 2014. The entire contents of the specification of Japanese patent application No. 2014-223651 filed on Oct. 31, 2014 are incorporated herein by reference.

EXAMPLES

The present invention is hereinafter described in more detail in the following by way of Examples, however, the present invention is not limited to the following Examples, and modifications which do not depart from the spirit and scope of the present invention are allowed and embraced within the technical scope of the present invention. Hereinafter, "part" and "%" mean "part by mass" and "% by mass", respectively, unless otherwise noted.

Measurement methods used in examples of the present invention are as follows.

Measurement of Contact Angle

The contact angle of a transparent film surface to water was measured by a θ/2 method with a liquid amount set to 3 μL using "DM 700" manufactured by Kyowa Interface Science Co., LTD.

A sample having a contact angle change ratio of not less than −27% after a light resistance test or having a contact angle change ratio of not less than −15% after a heat resistance test was evaluated as ○, and a sample that did not satisfy this condition was evaluated as x.

Measurement of Abrasion Resistance

A steel wool tester (manufactured by Daiei Seiki Co., Ltd.) provided with a HB pencil with an eraser (MITSUBI-SHI PENCIL CO., LTD.) was used. An abrasion test was conducted by applying a load of 500 g with the eraser while in contact with the transparent film, and the number of abrasion times was counted until the contact angle became −15° or less with respect to the initial contact angle.

Liquid Droplet Slide Behavior

The amount of 3 μL of a liquid droplet was placed on a transparent film surface, and the sliding state of the liquid droplet was evaluated at inclination of the transparent film from horizontal angle to an angle of 90 by sensory evaluation. Evaluation criteria are as follows.

☉: sliding very well; ○: sliding; Δ: feeling unsmooth; x: not sliding

Sense of Touch/Finger Slide Behavior

A transparent film surface was rubbed with a finger, and sense of touch/finger slide behavior was evaluated by sensory evaluation. Evaluation criteria are as follows.

☉: sliding very well; ○: sliding; Δ: feeling unsmooth; x: not sliding

Synthesis Example 1

The 0.86 g of sodium hydroxide was added to 13.4 g of tetraethyl orthosilicate (tetraethoxysilane), and the mixture was stirred at room temperature for 2 hours. While the obtained solution was cooled to −40° C. with dry ice, 4.12 g of a compound 1 represented by the following formula was added dropwise after diluted with heptane by 0.4 times.

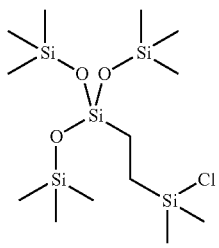

The obtained solution was filtered, and heptane was distilled off from the filtrate to obtain a compound 1 represented by the following formula.

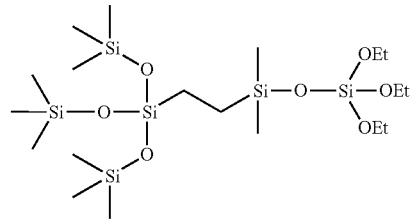 [SMILES: CCO[Si](OCC)(OCC)O[Si](C)(C)CC[Si](O[Si](C)(C)C)(O[Si](C)(C)C)O[Si](C)(C)C]

Synthesis Example 2

A three-neck flask was charged with 4.8 g of trimethylsilanol and 56 ml of tetrahydrofuran (THF), and purged with nitrogen. The mixture was cooled to −40° C., and 33.6 mL of a solution of n-butyllithium (n-BuLi) in hexane (1.6 mol/L) was added dropwise. The mixture was stirred for 15 minutes, and brought back to room temperature to obtain a precursor solution. A three-neck flask was charged with 20 g of 1,7-dichlorooctamethyltetrasiloxane and 80 mL of THF, and the mixture was cooled to −30° C., and the precursor solution was added dropwise. The mixture was stirred for 2 hours, then concentrated at 30° C. at 140 hPa, and then washed with hexane. The concentrate was distilled at 74.9° C. to 82.4° C. at 6 hPa, and the distillate (precursor 2) was collected.

A three-neck flask was charged with 7.74 g of tetraethoxysilane (TEOS) and 0.5 g of sodium hydroxide, and the mixture was stirred to dissolve sodium hydroxide. The TEOS was distilled off at 50° C. at 1.3 hPa. While the mixture was cooled to −50° C., 5.0 g of the precursor 2 dissolved in 7.4 mL of heptane was added dropwise. The obtained reaction product was filtered, and heptane was distilled off at 50° C. at 6 hPa to obtain a compound 2 represented by the following formula.

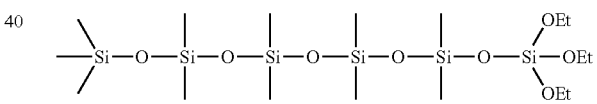

Synthesis Example 3

A three-neck flask equipped with a condenser was charged with 3.94 g of trichloroisocyanuric acid, and purged with nitrogen. Into the flask charged was 50 mL of dichloromethane through a septum, the mixture was stirred, and 5.0 g of tris(trimethylsiloxy)silane was added. The mixture was stirred for 1 hour, and then filtered. The filtrate was added dropwise while the filtrate was cooled in an ice bath charged with 150 mL of diethyl ether, 50 mL of ion-exchanged water and 1.87 g of triethylamine. The mixture was stirred at room temperature for 1 hour. The mixture was washed with ion-exchanged water, dehydrated with magnesium sulfate, and concentrated at 25° C. at 150 mmHg to obtain 5.8 g of an intermediate 3 of interest (silanol 1).

A three-neck flask was charged with 0.63 g of the intermediate 3 (silanol 1) and 1.68 g of THF, and the mixture was stirred. The mixture was cooled to −40° C., and 1.25 mL of a solution of n-BuLi in hexane (1.6 mol/L) was added dropwise. The mixture was heated to 0° C., 1.33 g of hexamethylcyclosilosixane dissolved in 4.11 g of THF was added dropwise, and the mixture was stirred for 12 hours.

The mixture was cooled to −40° C., and 0.4 g of chlorotriethoxysilane dissolved in 1.78 g of THF was added dropwise. To the mixture added was 50 mL of hexane, and the mixture was filtered. The filtrate was concentrated at 25° C. at 130 hPa to obtain a compound 3 represented by the following formula.

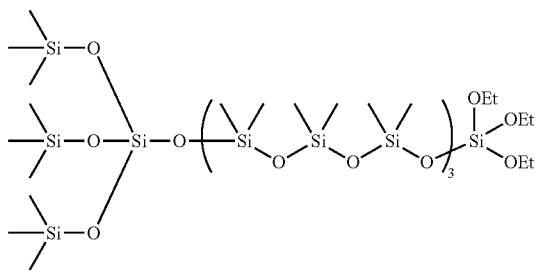

Synthesis Example 4

An intermediate 3 (silanol 1) was obtained in the same manner as in Synthesis Example 3. A three-neck flask was charged with 1.88 g of the intermediate 3 (silanol 1) and 5.04 g of THF, and the mixture was stirred. The mixture was cooled to −40° C., and 3.75 mL of a solution of n-BuLi in hexane (1.6 mol/L) was added dropwise. The mixture was heated to 0° C., 10.68 g of hexamethylcyclosiloxane dissolved in 12.32 g of THF was added dropwise, and the mixture was stirred for 17 hours. The mixture was cooled to −40° C., and 1.19 g of chlorotriethoxysilane dissolved in 5.33 g of THF was added dropwise. To the mixture added was 150 mL of hexane, and the mixture was filtered. The filtrate was concentrated at 25° C. at 130 hPa to obtain 13.11 g of a compound 4 represented by the following formula.

The results of $^1$H-NMR measurement (400 MHz, control: CHCl$_3$ (=7.24 ppm)) for the obtained compound 4 are shown below.

$^1$H-NMR (solvent: CDCl$_3$) δ (ppm): 0.08-0.1 ((CH$_3$)$_3$—Si)), 0.02-0.06 ((CH$_3$)$_2$—Si)), 3.6-4.0 (Si—O—CH$_2$), 1.1-1.3 (Si—O—CH$_2$CH$_3$)

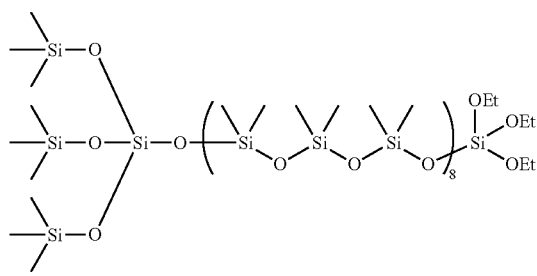

Example 1

To 3.88 mL (3.12 g) of methyl ethyl ketone as the solvent (c) added were 2.5×10$^{-4}$ mol (0.14 g) of the compound 1 as the organosilicon compound (a), 5×10$^{-3}$ mol (1.04 g) of tetraethyl orthosilicate (tetraethoxysilane) as the metal compound (b), and 200 μL of a solution of ethyl acetoacetate aluminum diisopropylate in 25% isopropyl alcohol (obtained by diluting "ALCH-75" manufactured by Kawaken Fine Chemicals Co., Ltd. by 3 times) as the catalyst (d), and the mixture was stirred for 24 hours to prepare a sample solution 1.

Examples 2 to 4

Sample solutions 2 to 4 were prepared in the same manner as in Example 1 except that the solvent (c), the organosilicon compound (a), the metal compound (b) and the catalyst (d) were as shown in Table 1.

Comparative Example 1

Octyltriethoxysilane (0.5 mL), 7.05 mL of tetraethyl orthosilicate, 9.5 mL of 0.01 M hydrochloric acid and 17 mL of ethanol were mixed. The obtained mixed liquid was diluted with ethanol by 8 times to obtain a comparative sample solution 1.

Comparative Example 2

OPTOOL DSX-E (0.2 g) (manufactured by DAIKIN INDUSTRIES, LTD.) and 39.8 g of Novec 7200 (manufactured by 3M Limited) were stirred at room temperature to obtain a comparative coating solution 2.

TABLE 1

| | | | Example | | | | Comparative Example | |
| --- | --- | --- | --- | --- | --- | --- | --- | --- |
| | | | 1 | 2 | 3 | 4 | 1 | 2 |
| | Sample Solution No. | | 1 | 2 | 3 | 4 | Comparative 1 | Comparative 2 |
| Organosilicon Compound (a) | Compound 1 | mol | 2.5 × 10$^{-4}$ | | | | | |
| | 561.1 g/mol | g | 0.14 | | | | | |
| | Compound 2 | mol | | 2.4 × 10$^{-4}$ | | | | |
| | 549.1 g/mol | g | | 0.13 | | | | |
| | Compound 3 | mol | | | 2.5 × 10$^{-4}$ | | | |
| | 1142.3 g/mol | g | | | 0.28 | | | |
| | Compound 4 | mol | | | | 8.9 × 10$^{-5}$ | | |
| | 2254.6 g/mol | g | | | | 0.2 | | |
| Metal Compound (b) | Tetraethoxysilane | mol | 5 × 10$^{-3}$ | 5 × 10$^{-3}$ | 2.7 × 10$^{-3}$ | 1.8 × 10$^{-3}$ | 7.05 mL | |
| | 208.3 g/mol | g | 1.04 | 1.12 | 0.56 | 0.38 | | |
| Solvent (c) | methyl ethyl ketone | mg | 3.1 | 3.6 | 1.6 | 6.3 | | |
| | ethanol | mL | | | | | 255 | |
| Catalyst Solution | a solution of ethyl acetoacetate aluminum diisopropylate in 25% isopropyl alcohol diluted by 3 times | μL | 200 | 50 | | | | |
| | 0.01 mol/L hydrochloric acid | mL | | | 0.56 | 3.8 | 9.5 | |
| Solvent (c) | Isopropyl alcohol | μg | 143 | 36 | | | | |

TABLE 1-continued

|  |  |  |  | Example | | | | Comparative Example | |
|---|---|---|---|---|---|---|---|---|---|
|  |  |  |  | 1 | 2 | 3 | 4 | 1 | 2 |
| Catalyst (d) | Water | | mg | | | 0.36 | 2.4 | 6 | |
|  | Ethyl acetoacetate aluminum diisopropylate | | μg | 13 | 3.3 | | | | |
|  | Hydrogen chrolide | | mg | | | 0.20 | 1.4 | 3.5 | |
| Comparative Compound | Octyl triethoxysilane | | mL | | | | | 0.5 | |
|  | DSX-E | | g | | | | | | 0.2 |
|  | Novec7200 | | g | | | | | | 39.8 |
| molar ratio (metal compound (b)/organosilicon compound (a)) | | | | 20.0 | 20.8 | 10.8 | 20.2 | | |
| weight ratio (solvent (c)/(organosilicon compound (a) + metal compound (b)) × 100 | | | | 0.2748 | 0.2909 | 0.2333 | 1.500 | | |
| weight ratio (catalyst (d)/(organosilicon compound (a) + metal compound (b)) × 100 | | | | 0.0011 | 0.00026 | 0.024 | 0.24 | | |

Weather Resistance Test (Light Resistance Test/Heat Resistance Test)

The sample solution 1, 3, 4 or the comparative sample solution 1 was applied to an alkali-treated glass substrate ("EAGLE XG" manufactured by Corning Incorporated) by spin coating under the condition of 3000 rpm and 20 seconds using a spin coater (manufactured by MIKASA Corporation), the resulting product was placed at room temperature for 1 day, and then cured at 120° C. to obtain a transparent film of the present invention, or a film of the comparative example.

The contact angle, the abrasion resistance, the slide behavior of liquid droplet and sense of touch/finger slide behavior for each of the obtained coating films are shown in Table 1.

Using a xenon acceleration exposure apparatus ("CPS+" manufactured by ATLAS), a light resistance test was conducted by irradiating the obtained transparent film with the lamp intensity adjusted at 250 W and the chamber inside temperature adjusted at 50 to 60° C. for 100 hours. A heat resistance test was conducted by incubating the obtained transparent film at 200° C. for 24 hours. The abrasion resistance, the slide behavior of liquid droplet and the sense of touch/finger slide behavior are shown in Table 2. The contact angle and contact angle change ratio before and after the weather resistance test for each of the films are shown in Tables 2 and 3.

TABLE 2

|  |  |  | Example 1 | Comparative Example 1 |
|---|---|---|---|---|
| Initial State | contact angle | ° | 102.7 | 101.5 |
|  | abration resistance | times | 150 | 200 |
|  | liquid droplet slide behavior | | ○ | ◎ |
|  | sense of touch/slide behavior | | ◎ | ○ |
| Light Resistance | contact angle | ° | 101.6 | 85.7 |
|  | change ratio $D_L$ | % | −1.1 | −15.6 |
|  | abration resistance | times | 150 | 150 |
|  | liquid droplet slide behavior | | ○ | X |
|  | sense of touch/slide behavior | | ◎ | X |
| Heat Resistance | contact angle | ° | 80.7 | 73.5 |
|  | change ratio $D_L$ | % | −21.4 | −27.5 |

TABLE 3

|  |  |  | Example | |
|---|---|---|---|---|
|  |  |  | 3 | 4 |
| Initial State | contact angle | ° | 102.1 | 100.4 |
| Light Resistance | contact angle | ° | 100.5 | 98.3 |
|  | change rate $D_L$ | % | −1.6 | −2.1 |
| Heat Resistance | contact angle | ° | 100.3 | 88.9 |
|  | change rate $D_H$ | % | −1.8 | −11.5 |

Mercury Lamp Irradiation Test

The sample solutions 2 and 3 were diluted with methyl ethyl ketone by 30 times to obtain coating solutions 2 and 3, respectively. The sample solution 4 was diluted with methyl ethyl ketone by 20 times to obtain a coating solution 4.

The coating solution 2, 3, 4 or the comparative coating solution 2 was applied to an alkali-treated glass substrate ("EAGLE XG" manufactured by Corning Incorporated) by spin coating under the condition of 3000 rpm and 20 seconds using a spin coater (manufactured by MIKASA Corporation), the resulting product was placed at room temperature for 1 day, and then cured at 120° C. to obtain a transparent film of the present invention, or a film of the comparative example.

A uniform photoirradiation unit (manufactured by USHIO INC.) was attached to a mercury lamp ("SP-9 250DB" manufactured by USHIO INC.), and a sample was placed at a distance of 17.5 cm from a lens. The light intensity at 200 to 800 nm was measured using an intensimeter ("VEGA" manufactured by OPHIL LTD.), and the result showed that the light intensity was 200 mW/cm². The sample was irradiated with light from a mercury lamp under an air atmosphere at a temperature of 20 to 40° C. and a humidity of 30 to 75% for 4 hours or 6 hours. The contact angle change ratio before and after irradiation is shown in Table 3, which is calculated on the basis of the following formula where $A_1$ is an initial contact angle of a liquid droplet on the transparent film and $B_z$ is a contact angle of the liquid droplet after irradiation.

The spectral irradiance for the mercury lamp ("SP-9 250DB" manufactured by USHIO INC.) is as shown in FIG. 1, and the mercury lamp has an emission line in a wavelength region of not more than 300 nm.

contact angle change ratio (%)={$(B_z-A_1)/A_1$}×100 (%)

TABLE 4

| | | | Experiment | | | Comparative Experiment |
|---|---|---|---|---|---|---|
| | | | 2 | 3 | 4 | 2 |
| contact angle change rate | 4 hours | % | −2.5 | −2.7 | −4.9 | −9.6 |
| | 6 hours | % | −15.0 | −4.4 | −8.0 | −18.0 |

INDUSTRIAL APPLICABILITY

The transparent film of the present invention attains water/oil repellency as well as heat resistance and light resistance (weather resistance), and is useful as a substrate in display devices such as touch panel displays, optical elements, semiconductor elements, building materials, automobile components, nanoimprint techniques and so on.

The invention claimed is:

1. A transparent film comprising:
a polysiloxane backbone;
a trialkylsilyl containing molecular chain bonded to a part of silicon atoms forming the polysiloxane backbone, wherein the number of elements forming the trialkylsilyl containing molecular chain is not less than 50,
alkyl groups in the trialkylsilyl containing molecular chain may be replaced by fluoroalkyl groups; and
a unit including a metal atom and a group bonded to the metal atom selected from a siloxane containing group and hydroxy group, wherein the metal atom is selected from trivalent and tetravalent metal atoms capable of forming a metal alkoxide, the number of elements in the siloxane containing group is smaller than the number of elements in the molecular chain of the trialkylsilyl containing molecular chain, and the unit is bonded to the polysiloxane backbone at a position of the metal atom,
wherein the difference in the number of elements between the trialkylsilyl containing molecular chain and the siloxane containing group is not less than 20, and
the transparent film satisfies at least one of the relationships of:

$(B_H - A_0)/A_0 \times 100(\%) \geq -27(\%)$; and $(B_L - A_0)/A_0 \times 100(\%) \geq -15(\%)$, provided that $A_0$ is an initial contact angle of a liquid droplet on the transparent film, $B_H$ is a contact angle of a liquid droplet on the transparent film incubated at 200° C. for 24 hours, and $B_L$ is a contact angle of a liquid droplet on the transparent film irradiated by a xenon lamp with an intensity of 250 W for 100 hours.

2. The transparent film according to claim 1, wherein the trialkylsilyl containing molecular chain is represented by a formula (s1) below:

$*—R^{s2}Si(R^{s1})_3$ (s1)

wherein each of $R^{s1}$ independently represents a hydrocarbon group or a trialkylsilyloxy group, provided that these hydrocarbon groups are alkyl groups when all $R^{s1}$ are hydrocarbon groups;
$R^{s2}$ represents a dialkylsiloxane chain and an oxygen atom in the dialkylsiloxane chain may be replaced by a divalent hydrocarbon group and a part of methylene groups (—CH$_2$—) in the divalent hydrocarbon group may be replaced by oxygen atoms; and
* represents a bond with silicon atom.

3. The transparent film according to claim 2, wherein the trialkylsilyl containing molecular chain is represented by a formula (s1-1) below:

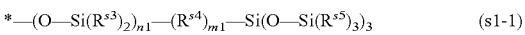

$*—(O—Si(R^{s3})_2)_{n1}—(R^{s4})_{m1}—Si(O—Si(R^{s5})_3)_3$ (s1-1)

wherein each of IV independently represents an alkyl group with a carbon number of not less than 1 and not more than 4;
$R^{s4}$ represents a divalent hydrocarbon group with a carbon number of not less than 1 and not more than 10, and a methylene group (—CH$_2$—) in $R^{s4}$ may be replaced by an oxygen atom;
each of $R^{s5}$ independently represents an alkyl group with a carbon number of not less than 1 and not more than 4;
m1 and n1 independently represent an integer of not less than 0; and
* represents a bond with silicon atom;
provided that occurrence order of the repeating units parenthesized with the subscripts of n1 and m1 is arbitrary in the formula.

4. The transparent film according to claim 2, comprising a structure (B) represented by a formula (2-I) below:

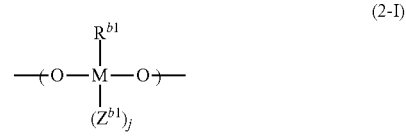

(2-I)

wherein $R^{b1}$ represents the siloxane containing group, hydroxy group or —O— group;
$Z^{b1}$ represents a hydrolyzable group, hydroxy group or —O— group, and $R^{b1}$ and $Z^{b1}$ may be the same or different among a plurality of formulae (2-I);
M represents the trivalent or tetravalent metal atom capable of forming the metal alkoxide; and
j represents an integer of 0 or 1 depending on M.

5. The transparent film according to claim 4, wherein M represents Al, Si, Ti or Zr.

6. The transparent film according to claim 5, wherein M represents Si.

7. The transparent film according to claim 1, comprising a structure (B) represented by a formula (2-I) below:

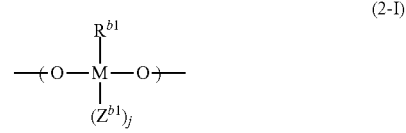

(2-I)

wherein $R^{b1}$ represents the siloxane containing group, hydroxy group or —O— group;
$Z^{b1}$ represents a hydrolyzable group, hydroxy group or —O— group, and $R^{b1}$ and $Z^{b1}$ may be the same or different among a plurality of formulae (2-I);
M represents the trivalent or tetravalent metal atom capable of forming the metal alkoxide; and
j represents an integer of 0 or 1 depending on M.

8. The transparent film according to claim 7, wherein M represents Al, Si, Ti or Zr.

9. The transparent film according to claim 8, wherein M represents Si.

10. The transparent film according to claim 7, wherein an abundance ratio of the structure (B) to a structure (A) as structure (B)/structure (A) is not less than 0.1 and not more than 80 in terms of moles
wherein structure (A) comprises a trialkylsilyl containing molecular chain bonded to a silicon atom.

11. The transparent film according to claim 1, wherein the initial contact angle of the liquid droplet on the transparent film is not less than 95°.

12. A transparent film comprising:
a polysiloxane backbone;
a trialkylsilyl containing molecular chain bonded to a part of silicon atoms forming the polysiloxane backbone, wherein the number of elements forming the trialkylsilyl containing molecular chain is not less than 50,
alkyl groups in the trialkylsilyl containing molecular chain may be replaced by fluoroalkyl groups; and
a unit including a metal atom and a group bonded to the metal atom selected from a siloxane containing group and hydroxy group, wherein the metal atom is selected from trivalent and tetravalent metal atoms capable of forming a metal alkoxide, the number of elements in the siloxane containing group is smaller than the number of elements in the molecular chain of the trialkylsilyl containing molecular chain, and the unit is bonded to the polysiloxane backbone at a position of the metal atom,
wherein the difference in the number of elements between the trialkylsilyl containing molecular chain and the siloxane containing group is not less than 20, and
the transparent film satisfies a relationship represented by a formula below:

$$(B_{z1}-A_1)/A_1 \times 100(\%) \geq -9(\%)$$

provided that $A_1$ is an initial contact angle of a liquid droplet on the transparent film, and $B_{z1}$ is a contact angle of the liquid droplet on the transparent film irradiated by a mercury lamp having an emission line in a region of not more than 300 nm with an intensity at an irradiated surface of 200±10 mW/cm² at a temperature of 20 to 40° C. and a humidity of 30 to 75% for 4 hours under an air atmosphere.

13. The transparent film according to claim 12, wherein the trialkylsilyl containing molecular chain is represented by a formula (s1) below:

$$*-R^{s2}-Si(R^{s1})_3 \quad (s1)$$

wherein each of $R^{s1}$ independently represents a hydrocarbon group or a trialkylsilyloxy group, provided that these hydrocarbon groups are alkyl groups when all $R^{s1}$ are hydrocarbon groups;
$R^{s2}$ represents a dialkylsiloxane chain and an oxygen atom in the dialkylsiloxane chain may be replaced by a divalent hydrocarbon group and a part of methylene groups (—CH₂—) in the divalent hydrocarbon group may be replaced by oxygen atoms; and
* represents a bond with silicon atom.

14. A coating composition comprising an organosilicon compound (a) and a metal compound (b),
wherein the organosilicon compound (a) comprises at least one trialkylsilyl containing molecular chain and at least one hydrolyzable group bonded to a silicon atom, and
the metal compound (b) is a compound represented by a formula (II-1) below:

wherein M represents a trivalent or tetravalent metal atom capable of forming a metal alkoxide;
each of $A^{b1}$ independently represents a hydrolyzable group;
$Z^{b2}$ represents a siloxane containing group, a hydrocarbon chain-containing group or a hydrolyzable group;
$R^{b2}$ represents a siloxane containing group, a hydrocarbon chain-containing group or a hydrolyzable group, $R^{b2}$ and $Z^{b2}$ may be the same or different when $R^{b2}$ and $Z^{b2}$ represent a siloxane containing group or a hydrocarbon chain-containing group, and $R^{b2}$ and $A^{b1}$ may be the same or different when $Z^{b2}$ represents a hydrolyzable group, and $R^{b2}$ and $Z^{b2}$ may be the same or different among a plurality of formulae (II-1);
k represents an integer of 0 or 1 depending on M; and
wherein the siloxane containing group comprises elements in a number smaller than the number of elements forming the trialkylsilyl containing molecular chain in the organosilicon compound (a) when $R^{b2}$ represents a siloxane containing group,
wherein the difference in the number of elements between the trialkylsilyl containing molecular chain and the siloxane containing group is not less than 20.

15. The coating composition according to claim 14, wherein a molar ratio of the metal compound (b) to the organosilicon compound (a) as metal compound (b)/organosilicon compound (a) is not less than 10.

16. The coating composition according to claim 14, wherein the organosilicon compound (a) is represented by a formula (I-I) below:

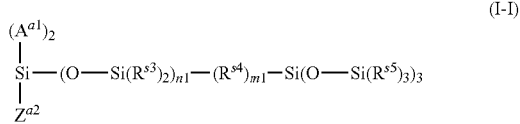

wherein each of $A^{a1}$ independently represents the hydrolyzable group;
$Z^{a2}$ represents a trialkylsilyl containing molecular chain, a hydrocarbon chain-containing group, a siloxane containing group or a hydrolyzable group, and $Z^{a2}$ and $A^{a1}$ may be the same or different when $Z^{a2}$ represents a hydrolyzable group, and $A^{a1}$ and $Z^{a2}$ may be the same or different among a plurality of formulae (I-I);
each of $R^{s3}$ independently represents an alkyl group with a carbon number of not less than 1 and not more than 4;
$R^{s4}$ represents a divalent hydrocarbon group with a carbon number of not less than 1 and not more than 10, and a methylene group (—CH₂—) in $R^{s4}$ may be replaced by an oxygen atom;
each of $R^{s5}$ independently represents an alkyl group with a carbon number of not less than 1 and not more than 4; and
m1 and n1 independently represent an integer of not less than 0;

provided that occurrence order of the repeating units parenthesized with the subscripts n1 and m1 is arbitrary in the formula.

17. A compound represented by a formula (I-I) below:

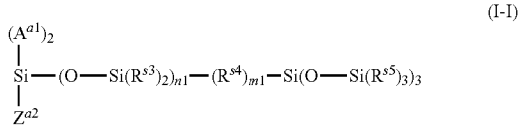
(I-I)

wherein each of $A^{a1}$ independently represents a hydrolyzable group;

$Z^{a2}$ represents a trialkylsilyl containing molecular chain, a hydrocarbon chain-containing group, a siloxane containing group or a hydrolyzable group, and $Z^{a2}$ and $A^{a1}$ may be the same or different when $Z^{a2}$ represents a hydrolyzable group, and $A^{a1}$ and $Z^{a2}$ may be the same or different among a plurality of formulae (I-I);

each of $R^{s3}$ independently represents an alkyl group with a carbon number of not less than 1 and not more than 4;

$R^{s4}$ represents a divalent hydrocarbon group with a carbon number of not less than 1 and not more than 10, and a methylene group ($-CH_2-$) in $R^{s4}$ may be replaced by an oxygen atom;

each of $R^{s5}$ independently represents an alkyl group with a carbon number of not less than 1 and not more than 4;

m1 and n1 independently represent an integer of not less than 0;

the number of elements forming $-(O-Si(R^{s3})_2)_{n1}-(R^{s4})_{m1}-Si(O-Si(R^{s5})_3)_3$ is not less than 50;

provided that occurrence order of the repeating units parenthesized with the subscripts of n1 and m1 is arbitrary in the formula; and the compound satisfies at least one of the following requirements (i) and (ii):

(i) m1 represents an integer not less than 3, $R^{s4}$ represents methylene group ($-CH_2-$) and $(R^{s4})_{m1}$ contains at least one $-CH_2-O-CH_2-$ moiety, and (ii) n1 represents an integer of not less than 1.

* * * * *